United States Patent [19]

Maltby et al.

[11] 4,146,834
[45] Mar. 27, 1979

[54] ADMITTANCE MEASURING SYSTEM FOR MONITORING THE CONDITION OF MATERIALS

[75] Inventors: Frederick L. Maltby, Jenkintown; Jonathan Kramer; Kenneth M. Loewenstern, both of Warminster, all of Pa.

[73] Assignee: Drexelbrook Controls, Inc., Horsham, Pa.

[21] Appl. No.: 743,618

[22] Filed: Nov. 22, 1976

Related U.S. Application Data

[63] Continuation-in-part of Ser. No. 507,540, Sep. 19, 1974, Pat. No. 3,993,947.

[51] Int. Cl.² .................... G01R 11/52; G01R 27/26
[52] U.S. Cl. .................. 324/60 R; 324/58 R; 324/57 R; 324/58.5 A; 324/58 A
[58] Field of Search ............... 324/60 R, 61 R, 57 R, 324/58 R, 58 A, 58.5, 58.5 A; 328/160, 158

[56] References Cited

U.S. PATENT DOCUMENTS

| 3,626,285 | 8/1969 | Hartke | 324/60 R |
| 3,648,165 | 3/1972 | Shawhan | 324/60 R |
| 3,746,975 | 7/1973 | Maltby | 324/61 R |
| 3,778,705 | 12/1973 | Maltby | 324/61 R |
| 3,805,156 | 4/1974 | Norton et al. | 324/61 R |

Primary Examiner—Saxfield Chatmon, Jr.
Attorney, Agent, or Firm—Woodcock, Washburn, Kurtz & Mackiewicz

[57] ABSTRACT

A two-wire transmitter includes an admittance sensing probe adapted to sense the conditions and corresponding admittance of materials. The probe is coupled into an admittance responsive network which generates an admittance signal representing the condition of materials. The output current from the transmitter is varied in response to the admittance signal. In one embodiment of the invention, the admittance responsive network comprises a variable frequency oscillator whose frequency varies with the admittance of the materials. In another embodiment, the admittance responsive network comprises a ramp generator with a frequency which varies with the admittance of the materials. In another embodiment, the admittance responsive network comprises a bridge whose balance changes in response to the admittance of the materials.

35 Claims, 27 Drawing Figures

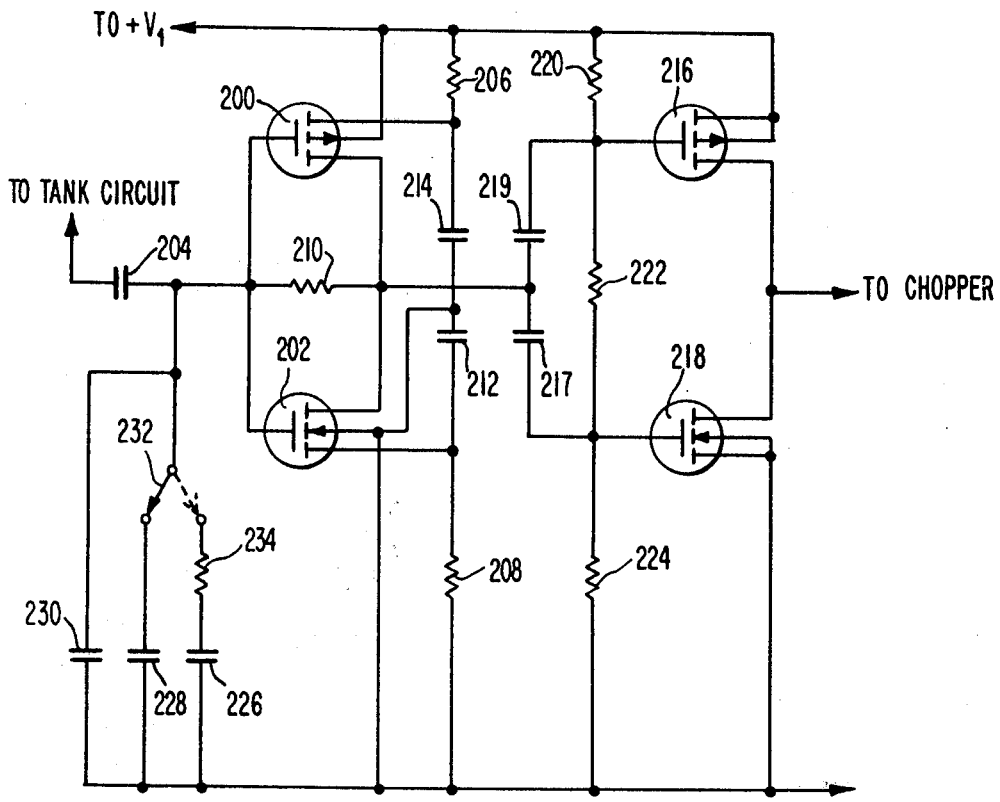
*Fig. 3*
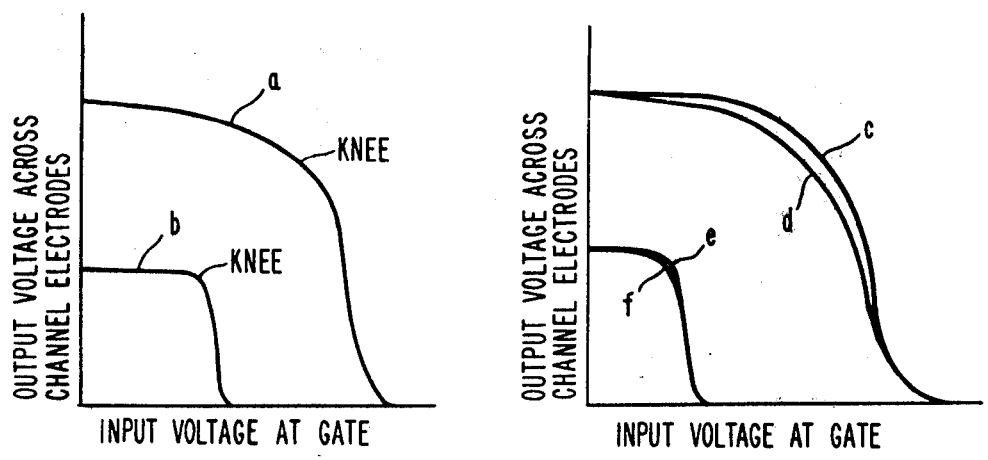
*Fig. 3a*     *Fig. 3b*

ADMITTANCE MEASURING SYSTEM FOR MONITORING THE CONDITION OF MATERIALS

RELATED APPLICATION

This is a continuation-in-part of application Ser. No. 507,540 filed Sept. 19, 1974, now U.S. Pat. No. 3,993,947.

BACKGROUND OF THE INVENTION

This invention relates to RF admittance measuring systems for monitoring the condition of materials, and more particularly, to systems of this type which are adapted for use at remote locations.

Heretofore, two-wire transmitters have been utilized to monitor various conditions at a remote location. Typically, a two-wire transmitter at a remote location is connected in series with a power supply and a load at another location through two transmission wires. As the condition being monitored at the transmitter varies, the effective series resistance across the transmitter varies so as to produce a change in the current drawn by the transmitter which represents (e.g., is generally proportional to) the condition being monitored. A two-wire transmitter of this type is designed for low power consumption since the amount of power available to the transmitte from the remotely located power supply may be limited. Furthermore, certain applications may require that the two-wire transmitter be "intrinsically safe" so as to permit its use in the monitoring of conditions in an explosive environment. Under these circumstance, lower energy usually associated with lower power consumption becomes important so as to preclude the possibility of ignition and explosion.

Although the state of the art in two-wire transmitters is adequate for monitoring various types of conditions, the prior art technology with respect to the RF admittance measurement is deficient for two-wire transmitters for the following reasons.

When measuring the RF admittance between a probe electrode and a reference surface such as a grounded vessel, the resistance is parallel with the capacitance between the probe electrode and the grounded vessel becomes very important from a power consumption standpoint. Heretofore, it has generally been assumed that shunt resistance is sufficiently small in a sufficiently large number of applications so as to render the power provided by the 4 milliamp current in a 4–20 milliamp two-wire transmitter system insufficient to power the two-wire transmitter. In other words, the shunt resistance alone might consume more power than is available at the 4 milliamp condition leaving little or no power to operate the circuitry of the transmitter. Also, power limitations exist where the admittance measuring circuit is battery-powered.

Moreover, in order for an admittance measurement to be accurate, reliable detection must be utilized. However, such reliability usually requires a substantial source of power which is inconsistent with the low power requirement of a two-wire transmitter as discussed above and the available power because of the shunt resistance. This combination of factors imposes severe restrictions on the power which is generally considered necessary to provide a reliable RF signal source. Similar restrictions are placed on the power generally considered necessary to assure that the detector operates with a high degree of reliability.

Another problem which is somewhat unqiue to admitance measurements is the isolation of the admittance responsive network in which the unknown admittance being measured is connected. Typically, the unknown admittance being measured is from a probe electrode to ground as disclosed in Maltby et al U.S. Pat. No. 3,781,672 and Maltby U.S. Pat. No. 3,706,980, both of which are assigned to the assignee of this invention. However, a power supply at a location remote from the admittance responsive network as in the case of a two-wire transmitter, may not be connected to ground in a manner compatible with the network. It is therefore necessary to isolate the admittance responsive network, or at least the admittance sensing probe, from the power supply so as to permit the network to be connected to ground regardless of the power supply circuit. This is also true of the admittance responsive networks employing a variable frequency oscillator such as that disclosed in Spaw U.S. Pat. No. 3,807,231. Moreover, if the voltage across the unknown admittance were reduced to minimize power consumption, the signal representing the changes in admittance of the admittance responsive network would require amplification. Accordingly, the problem exists of providing an isolated source of power for such amplification.

Other problems exist in assuring linear and stable calibration of the admittance measuring system. It is also important to provide a system which will work with various types of probes and various lengths of cables associated with the probes without adversely affecting the admittance measurement.

Another problem which can be quite troublesome is the low level of analog signals which may be generated by an admittance measuring system. Low level analog signals are particularly difficult to process if a high degree of accuracy is to be attained.

To a very large degree, the above-mentioned problems are encountered when the system for monitoring the condition of materials comprises a battery-operated unit as well as a two-wire transmitter. Under these circumstances, the available power is again limited.

SUMMARY OF THE INVENTION

It is an overall object of this invention to monitor the condition of materials at a remote location utilizing admittance measurements.

It is more specific object of this invention to minimize the power consumption necessary in making the admittance measurements.

It is also a more specific object of the invention to provide an intrinsically safe system for making the admittance measurements.

In accordance with these objects, a particularly preferred embodiment of the invention comprises a two-wire transmitter system including a power supply and a load at one location and a two-wire transmitter at another location interconnected by a pair of transmission lines carrying a variable signal current. An admittance sensing probe includes a probe electrode adapted to sense the conditions and corresponding admittance of the materials and an admittance responsive network coupled to the probe for generating an admittance signal representing the condition of the materials. Output means are coupled to the admittance responsive network for varying the signaling current through the pair of transmission lines in response to the admittance signal. The output means may comprise feedback means for generating a signal substantially proportional to the signaling current for comparison with the admittance signal.

In further accordance with these objects, the admittance responsive network may comprise a bridge wherein one side of the bridge comprises the admittance representing the condition of materials and the other side of the bridge comprises a reference admittance.

It is also a specific object of this invention to provide isolation between a floating power supply and the probe so as to permit the admittance of the materials to be measured between the sensing electrodes and a grounded member.

It is a further object of this invention to provide DC isolation which is not subject to high voltage breakdown.

It is another object of the invention to provide a regulated floating power supply for the admittance responsive network.

It is another object of the invention to provide an output means which maintains the stable current output for all current levels representing the admittance measurement.

In the preferred embodiment of the invention, the output means comprises an output amplifier including a voltage feedback network connected to a resistor through which the DC current drawn by the two-wire transmitter flows so as to stabilize the flow of the DC current at all current levels.

It is yet another object of this invention to provide a two-wire transmitter having a pair of terminals which may be interchangeably connected to the two transmission wires without damaging or adversely affecting the two-wire transmitter.

In accordance with this object of the invention, the input of the two-wire transmitter includes a full wave rectifying bridge permitting current flow through one pair of diodes when the terminals of the transmitter are connected to the transmission wires with one polarity and current flows through the other pair of diodes when the terminals of the transmitter are connected to the transmission wires with the opposite polarity.

It is also an object of this invention to provide for accuracy and linear calibration of the admittance measurement.

In accordance with this object of the invention, the admittance measuring means comprises a bridge network having the unknown admittance on one side of said bridge and a reference admittance on the other side of the bridge. The bridge further comprises means for zero and span calibration or adjustment.

It is a further object of this invention to provide for admittance measurements wherein the length of the cable connecting the probe electrode to the bridge network does not affect the measurement of the admittance.

In accordance with another object of this invention, the system may employ various types of probes including linear and non-linear immersion probes utilizing a guard electrode as well as a probe electrode.

In accordance with a still further object of this invention, the overall system is adapted for use in a battery operated mode or an AC supply mode.

It is another object of this invention to provide spark protection means.

In accordance with this object of the invention, spark protective devices are associated with the admittance responsive network.

In a particularly preferred embodiment of the invention, the admittance responsive network may comprise first oscillator means comprising a frequency determinative circuit coupled to the admittance sensing probe such that the first oscillator means generates a first frequency which changes in responses to changes in the admittance of the materials. A second oscillator means may generate a second signal having a substantially constant reference frequency. Frequency difference detector means are coupled to the first oscillator means and the second oscillator means with the output of the frequency detector means coupled to the output means for varying the signaling current in response to the difference in frequencies of the first oscillator means and the second oscillator means.

The portion of the first oscillator means comprising the admittance sensing probe may form one half of a bridge and a portion of the second oscillator means may include a reference admittance forming the second half of the bridge. A compensate terminal may be included in the second half of the bridge for connection of a compensating cable matched to a probe cable.

The frequency difference detector means may comprise means for digitizing a signal representing the difference in frequency between the first oscillator means and the second oscillator means.

In another embodiment of the invention, the admittance responsive network comprises first admittance means coupled to the admittance sensing probe so as to include the admittance of the materials and second admittance means comprising a reference admittance. A current source is coupled to the first admittance means and the second admittance means for alternate and periodic charging thereof and discharge means are also coupled to the first admittance means and the second admittance means for alternate and periodic discharging thereof. Charge rate detection means are coupled to the first admittance means and the second admittance means for detecting the different in charging rates therebetween.

The first admittance means and the second admittance means may comprise an admittance bridge where the first side of the bridge comprises the first admittance means and the second side of the bridge comprises the second admittance means and the charge rate detection means detects the difference in time to charge the first side as compared with the second side The output means may comprise modulator means coupled to the charge rate detection means for generating a signal representing the difference in charge rates. A demodulator means is AC coupled to the modulator means and isolated therefrom for demodulating the modulated signal and applying the demodulated signal to an output amplifier means which is coupled to the pair of transmission lines so as to control the current drawn by the two-wire transmitter.

In accordance with another important aspect of this embodiment, DC rather than RF operating controls are utilized to avoid the effects of stray coupling. More specifically, the operating controls are located in the current source and adjust the DC flow of current to said admittance bridge.

Although specific objects of the invention have been identified, other objects will be apparent from the drawings taken in conjunction with the specification.

BRIEF DESCRIPTION OF THE DRAWINGS

FIGS. 2(a-c) are waveform diagrams utilized in describing the operation of the circuit of FIG. 2;

FIG. 3 is a schematic circuit diagram of a chopper drive circuit embodying another important aspect of the invention;

FIGS. 3A and 3B are input voltage-output voltage transfer characteristic curves of the field effect transistors of FIG. 3;

FIGS. 12 (a & b) are schematic diagrams of circuitry shown in block form in FIG. 11 where the diagram has been split along line x—x;

DETAILED DESCRIPTION OF A PARTICULAR EMBODIMENT

Figure 1:
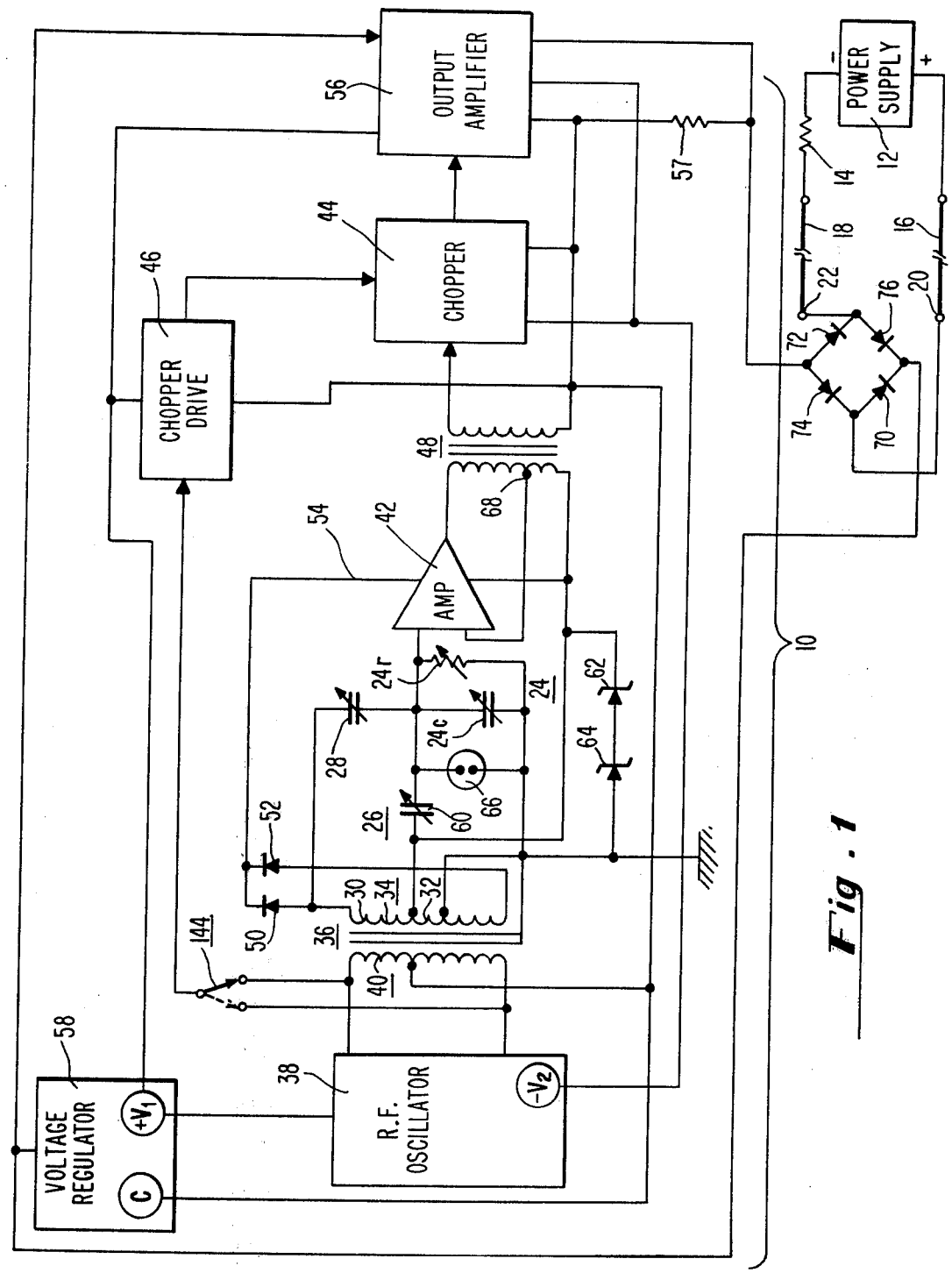
FIG. 1 is a block diagram of a two-wire transmitter embodying the invention.

As shown in FIG. 1, a two-wire transmitter 10 is connected in series with a power supply 12 and a load represented by a resistor 14 through transmission wires 16 and 18 connected to the terminals 20 and 22 of the two-wire transmitter 10. In accordance with this invention, the transmitter 10 is adapted to measure and draw a signal current representing an unknown measured admittance 24 which may represent the condition of materials sensed by the probe. The measured admittance 24 which represents the capacitance 24c and the resistance 24r from a probe electrode to ground forms one arm of a bridge network 26 also comprising a capacitor 28 and windings 30 and 32 of a secondary 34 in a transformer 36. The bridge network 26 is driven by an oscillator 38 having an output connected to the primary 40 of the transformer 36.

In accordance with this invention, the voltage across the admittance 34 is limited to a level so as to assure adequate power for the two-wire transmitter in view of the power consumption by the unknown resistance 24r. As will now be described in detail, the voltage is limited to less than $\sqrt{2V}$ where V is the voltage across the two-wire transmitter and the current drawn by the two-wire transmitter varies from 4–20 milliamps.

Heretofore, it has been assumed that the unknown resistance 24r of the unknown admittance 24 being measured may vary over a wide range. Of course, for a fixed voltage, if the resistance 24r should become very small, a good deal of power would be consumed in that resistance. In a conventional two-wire transmitter, the sole source of power is the current flow through the transmission wires 16 and 18 which is conventionally at levels of 4–20 milliamps. If it is assumed that the power supply produces an output voltage of 24 volts, the voltage across the terminals 20 and 22 of the two-wire transmitter may, for example, be 12 volts where the total voltage drop across the load 14 plus the drop across each of the wires 16 and 18 is 12 volts. This means that when the two-wire transmitter is drawing 4 milliamps, the total power available to operate the two-wire transmitter is P = VI = 48 milliwatts. This would mean that extremely small shunt resistances 24r would require extremely small voltages across the unknown admittance 24 to permit the two-wire transmitter to operate from the available power at the 4 milliamp level.

It has however been discovered, as will be described subsequently, that the resistance 24r, in almost all applications regardless of the type of probe utilized, will not fall below 500 ohms. Thus, by only moderately limiting the voltage across the unknown admittance 24 and thus the voltage across the unknown resistance 24r, sufficient power is available to the two-wire transmitter even at the 4 milliamp current level. Having once recognized that the magnitude of the resistance 24r will not, in almost all applications, fall below 500 ohms, the magnitude of the voltage across the resistance 24r may be readily computed for a 4–20 milliamp two-wire transmitter from the following equation:

$$(v^2/r_{24}) < VI_m \tag{1}$$

where

V = the voltage across the transmitter;

v = the rms voltage across resistance 24r;

$I_m$ = the minimum current flow through the two-wire transmitter 10; and $r_{24}$ = the resistance in ohms of the resistance 24. For $I_m$ equal 4 milliamps and $r_{24}$ equal 500 ohms, then $$v < \sqrt{2V} \tag{2}$$

If V equals 12 volts, then v is less than $\sqrt{24}$ or less than approximately 5 volts rms. Of course, the two-wire transmitter itself requires some power to operate. Therefore, in the preferred embodiment where $I_m = 4$ milliamps and V = 12 volts, v = approximately 2.2 volts rms, or substantially less than $\sqrt{2V}$.

In further accordance with this invention, the oscillator 38 of the class C type, i.e., the collector current of each of the two transistors in the oscillator 38 which drive the tank circuit flows through an angle less than 180° of the 360° cycle of the RF sinusoidal signal applied to the bridge network 26. However, class C operation may produce distortion in the intended sinusoidal signal. Therefore, in further accordance with this invention, the oscillator 38 comprises a resonant circuit in the form of a tank circuit including the transformer 36 as well as the measured admittance 24 as will subsequently be described in detail with reference to FIG. 2. Since the admittance 24 is part of the resonant circuit, little additional current is required to drive additional admittance between the probe and ground.

As also shown in FIG. 1, an AC error signal representing the unbalance of the bridge network 26 and thus the unknown measured admittance 24 is applied to an error amplifier 42. The error amplifier 42 permits the use of relatively low AC voltages in the bridge network 26 in accordance with this invention. The output from the error amplifier 42 is then applied to a phase sensitive detector comprising a chopper 44 which is triggered by a chopper drive 46.

In accordance with another important aspect of the invention, the bridge network 26 and the error amplifier 42 are isolated from the power supply by the first transformer 36 and the second transformer 48 which couples the output of the error amplifier 42 to the input of the chopper 44. In other words, the power supply is allowed to float with respect to the probe. This permits the use of a probe for measuring the admittance 24 between the probe electrode and ground without being concerned with the manner in which the power supply 12 is connected to ground. Note that this power supply 12 is at a remote location with respect to the two-wire transmitter 10 and the manner in which the power supply 12 is connected to ground may not be readily discernible at the two-wire transmitter 10. The isolation provided by the transformers 36 and 48 also allows either terminal 20 or 22 of the two-wire transmitter 10 to be maintained at a very substantial AC or DC voltage with respect to ground without any high voltage breakdown.

In order to provide isolation for the bridge network 26 while still providing a DC power supply for the error amplifier 42 which is directly coupled to the bridge network 24, diodes 50 and 52 are provided to rectify the RF sinusoidal signal from the secondary 34 of the transformer 36. Diodes 50 and 52 are then connected to a terminal 54 of the amplifier 42 so as to provide a DC power supply therefor which is isolated from the power supply 12.

In contrast, the DC power supply voltages for the RF oscillator 38, the chopper drive 46, the chopper 44 and an output amplifier 56 are provided by a voltage regulator 58 with a positive power supply terminal $+V_1$. In addition, a negative power supply voltage is provided by a voltage regulating circuit in the RF oscillator 38 at a terminal $-V_2$. The chopper drive 46, the chopper 44 and the output amplifier 56 are also connected to the circuit common terminal C of the voltage regulator 58.

In order to permit the bridge to be zeroed with a capacitance 24c from probe to ground which is different from the zeroing capacitance 28, the number of windings 30 differs from the number of windings 32. For example, the number of windings 30 may be three times as large as the number of windings 32 so as to allow the bridge to be zeroed when the measured capacitance 24c from probe to ground is three times as great as the zeroing capacitance 28. In addition, the bridge network 26 includes a variable span capacitor 60. By adjusting the span capacitor 60, the measured capacitance 24c necessary to produce a predetermined current through the transmission wires 16 and 18 may be varied. In addition, the output amplifier 56 may be provided with a gain adjustment which provides fine span control.

In order to provide spark protection for the transmitter 10, a pair of series connected, reversed poled Zener diodes 62 and 64 are connected between one terminal of the span capacitor 60 and ground. A neon bulb 66 is connected between the other terminal of the span capacitor 60 and ground. The protection afforded by the diodes 62 and 64 and the bulb 66 allow the transmitter 10 to withstand spikes of several thousand volts across the admittance 24 with no component failure or unbalancing of the bridge network 26.

As also shown in FIG. 1, a tap on the primary 68 of the transformer 48 is connected to the input of the error amplifier 42. This connection provides feedback to the amplifier 42 so as to control the gain thereof. Of course, changing the location of the tap 68 will change the gain of the amplifier 42 and thus the magnitude of the output applied to the chopper 44.

As the output from the chopper 44 varies and is compared with the voltage across a resistor 57 connected to the wire 22, the signal current output from the amplifier 56 is transmitted through the wires 16 and 18. The current having a magnitude which represents the admittance 24 and the condition of the materials being measured is utilized to drive the load 14.

In accordance with one aspect of the invention, the input of the two wire transmitter 10 comprises a full-wave rectifying bridge network comprising diode pairs 70 and 72 which conduct the 4–20 milliamp current when the terminal 20 is positive with respect to the terminal 22. Similarly, the pair of diodes 74 and 76 conduct when the terminal 22 is positive with respect to the terminal 20 or 22 to be connected to either transmission wire without damaging or affecting the operation of the transmitter.

The class C RF oscillator will now be described in detail with reference to FIG. 2. The oscillator comprises a multivibrator such as a pulsed amplifier including a pair or transistors 100 and 102 which are alternately conductive so as to drive a resonant tank circuit comprising the transformer 36 and a capacitor 104 which is connected in parallel with the primary 40 or the transformer 36 as well as the measured admittance A in the bridge network 26. The base drive for the transistor 100 of the multivibrator is provided by the capacitor 106 and resistors 108 and 110 where the resistor 110 is connected to a transistor 112 in a base current regulating circuit. Similarly, a capacitor 114 and resistors 116 and 118 provide a base drive for the transistor 102. The base current of the transistors 100 and 102 charge the capacitors 106 and 114 to a positive voltage higher than the supply voltage thereby cutting off the transistors 100 and 102 during most of the cycle so as to achieve class C operation. Diodes 120 and 122 which are connected in the base circuits of the transistors 100 and 102 respectively provide protection for the bases of the transistors by blocking current flow when the junction of the resistors 108 and 110 and the junction of the resistors 116 and 118 are driven positive.

As mentioned previously, the transistor 112 is part of a regulating circuit. The regulation afforded by the transistor 112 maintains the amplitude of the RF sinusoidal signals substantially constant despite any change in the operating characteristics of transistors within the oscillator and despite resistive loading due to the resistance 24r. In this connection, the base of the transistor 112 is connected to a tap in the voltage divider comprising resistors 124 and 126 with one terminal of the voltage divider connected to the $+V_1$ power supply terminal of the voltage regulator and the other terminal of the voltage divider connected to a capacitor 128 which is connected to circuit common through a discharge resistor 130 which may be potted with the capacitor 128 to provide intrinsic safety.

The capacitor 128 is charged to a negative potential with respect to circuit common by full wave rectifying diodes 127 and 129 connected across the tank circuit such that the tap of the voltage divider connected to the base of the transistor 112 is maintained at an operating point of approximately zero volts which is just enough to render the collector-emitter circuit of the transistor 112 conductive. The emitter of the transistor 112 is maintained slightly negative by a resistor 132 and a diode 134. Diode 134 compensates for the base emitter voltage of the transistor 112 and partially compensates for changes in the base emitter voltage of the transistor 112 with temperature so as to assure stable calibration. As clearly shown in FIG. 2, the negative voltage of the capacitor 128 is utilized to provide a negative power supply voltage $-V_2$ for the chopper 44 and the output amplifier 56 as shown in FIG. 1.

The regulating circuit as previously described including the transistor 112 operates in the following manner to maintain the amplitude of the RF sinusoidal signal at the transformer 36 substantially constant. The voltage across the transformer 36 which is the voltage across the tank circuit of the oscillator is, in effect, detected by the diodes 127 and 129 which charge the capacitor 128. The resulting negative DC voltage on the capacitor is then compared to the voltage of the regulator 48 at the resistive voltage divider comprising the resistors 124 and 126 so as to maintain the intermediate tap at approximately circuit common. As the characteristics of the transistors change with temperature and the probe is resistively loaded as respresented by the resistance 24r, the transistor 112 leaks bias off the capacitors 106 and 114 so as to maintain the amplitude of the oscillator and the corresponding voltage across the capacitor at the same potential.

In order to eliminate any distortion in the RF sinusoidal signal, a relatively large choke inductor 136 provides a high impedance load to the tank circuit thereby avoiding any sharp current pulse which might distort the RF sinusoidal waveform. An inductor 140 and a capacitor 142 provides a power supply filter network.

The class C mode of operation the oscillator 38 will now be described with reference to the waveforms of FIGS. 2 (a-c). As shown in FIG. 2a, the output voltage from the collector to circuit common which is applied across the primary 40 of the transformer 36 is substantially sinusoidal due to the resonant action of the primary 40 with the capacitor 104 and the image of the bridge capacitors 24c and 28 (shown on FIG. 6) reflected through transformer 40. However, the diode 120 is biased off by the voltage on capacitor 106 for most of the cycle, producing a voltage pulse as shown in FIG. 2c at the anode of diode 120. Thus, the collector current which flows through the transistor 100 is intermittent as shown in FIG. 2b. In fact, only a brief surge of collector current flows as shown in FIG. 2b during the 360 degree cycle depicted in FIG. 2a. (In actuality, some current continues to flow during the remainder of the cycle but this current is small relative to the surge of current flow and has not therefore been depicted in the drawing.) As shown in FIG. 2b, the substantial or surge of collector current flows for substantially less than 90 degrees of the 360 degree cycle which is of course substantially less than 180 degrees flow of current which still falls within the realm of class C operation. Note that the surge of current corresponds in time with the peak voltages for FIGS. 2a and 2c to assure that the maximum power is derived from the current flow.

Figure 2:
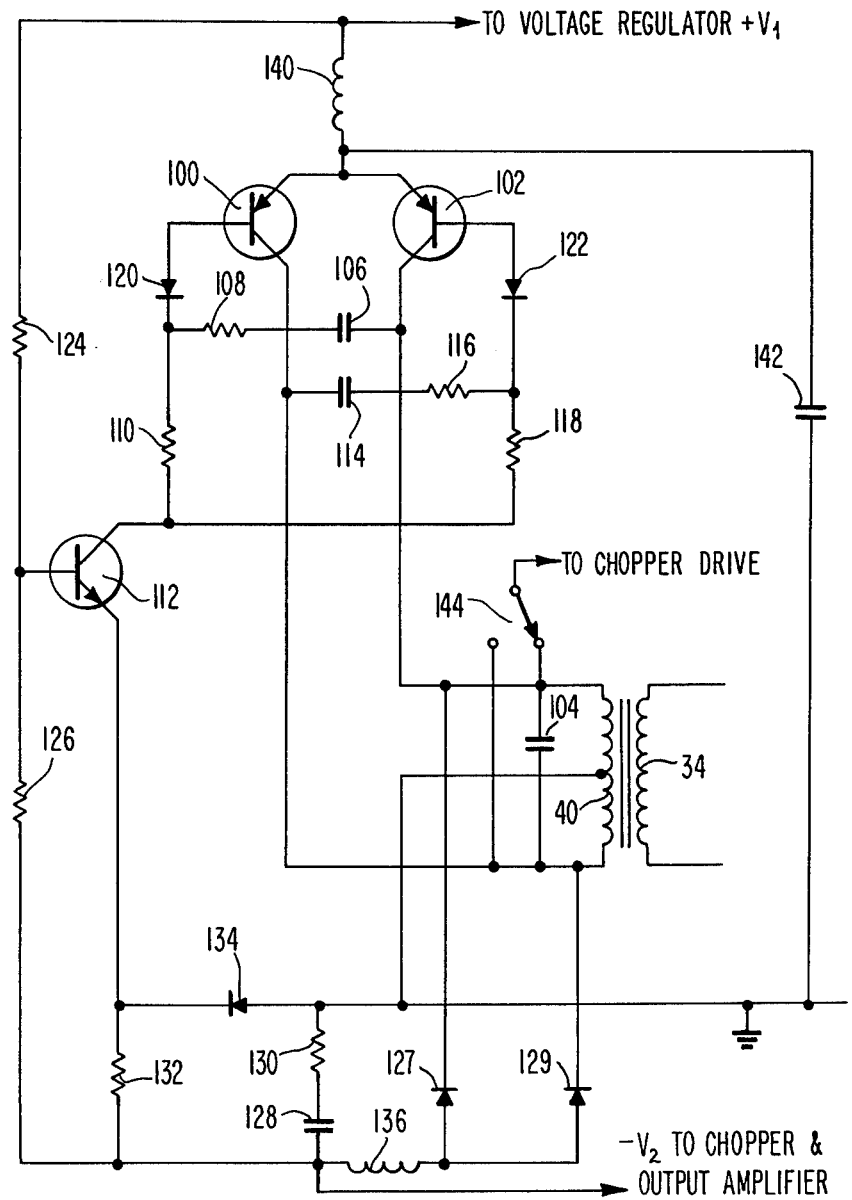
FIG. 2 is a schematic circuit diagram of an RF signal generator embodying one important aspect of the invention.
Figure 2A:
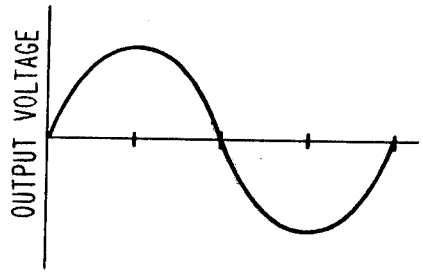
Figure 2B:
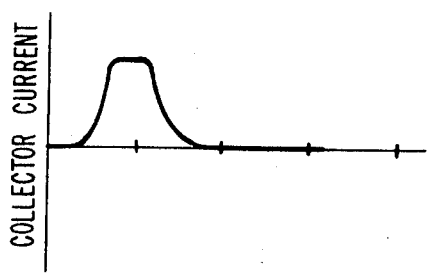
Figure 2C:
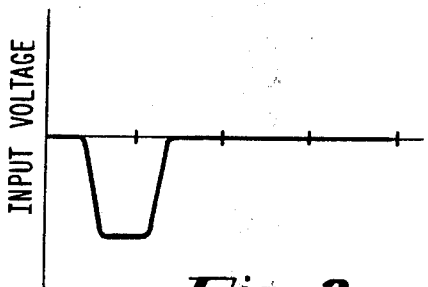

As shown in FIGS. 1 and 2, the tank circuit is connected to the chopper drive 46 through a switch 144 which is capable of connecting the chopper drive to either terminal of the primary 40. By moving the switch from one position to the other, the phase of the chopper drive is reversed 180 degrees and the phase sensitive detection performed by the chopper 44 is changed by 180 degrees to permit the transmitter to operate in a high level or low level failsafe mode. As will now be described in detail with reference to FIG. 3, the chopper drive 46 generates a square wave trigger signal for the chopper 44 while minimizing power consumption and optimizing stable, accurate calibration consistent with this invention.

To achieve these objectives, chopper drive 46 as shown in FIG. 3 comprises a first pair of field effect transistors 200 and 202 having gate electrodes connected to the tank circuit through a capacitor 204. The first channel (drain) electrodes of the transistors 200 and 202 are interconnected and the second channel (source) electrodes are connected between circuit common and the regulated supply voltage $+V_1$. In accordance with the objectives of this invention, the second channel electrodes are connected to the power supply voltage $+V_1$ and circuit common through resistors 206 and 208.

The sinusoidal output from the oscillator 38 as shown in FIG. 1 is applied to a capacitive divider network including the capacitor 204 and capacitors 228 and 230 connected between the capacitor 204 and circuit common. The capacitively divided sinusoidal signal across the capacitors 228 and 230 is then applied to the gate electrodes of the transistors 200 and 202 to alternately gate the transistors between the conductive states.

It will be understood that the resistors 206 and 208 play a particularly important role in assuring low power consumption and accuracy in the phase detection at the chopper 44. In this connection, it will be understood that the resistors 206 and 208 serve to limit the voltage across the channel electrodes of each of the transistors 200 and 202 which in turn sharpens the knee of the input voltage-output voltage transfer characteristics of the field effect transistors. As shown in curve a of FIG. 3a, large output voltages from channel-electrode-to-channel-electrode of a field effect transistor give a rounded knee to the output voltage-input voltage transfer characteristic while limiting the output voltage as shown in curve b sharpens the knee of the output voltage-input voltage characteristic. This tends to produce a more nearly square wave signal which is of the utmost importance in achieving reliability in the phase detection at the chopper 44.

Moreover, as shown in FIG. 3b, limiting the output voltage of channel electrode to channel electrode of the field effect transistor tends to immunize the field effect transistor to changes in the output voltage-input voltage transfer characteristic with temperature. As shown in waveforms c and d of FIG. 3b where curve c represents the output-input voltage characteristic at a temperature of $-55°$ C. and curve d represents the output-input voltage characteristic at a temperature of $+25°$ C. Thus, a large channel electrode-to-channel-electrode voltage makes for a very substantial difference in curves c and d which affect the stability of the calibrations for the system. On the other hand, limiting the output voltage as shown in curves e and f renders the $-55°$ C. curve e substantially identical to the $+25°$ C. curve f.

In addition, the channel resistors tend to limit current flow through the transistors 200 and 202 when the transistors 200 and 202 are simultaneously conductive between the first and second channel electrodes. This assures that the power consumption by the transistors 200 and 202 will not be excessive as in the case where both of the transistors 200 and 202 conduct simultaneously.

The output from the interconnected first channel electrodes is a square wave voltage riding above circuit common. In order to assure that the waveform is square, a feedback resistor 210 is provided between the first channel electrodes and the gate electrode so as to raise the gate electrode to the average DC voltage at the first channel electrodes. The resistor 210 assures a duty factor of 50% thereby compensating for small differences in the threshold voltages of the field effect transistors. Capacitors 212 and 214 provide a low impedance to drive the gate capacitance of the succeeding stage with the square wave signal generated by the field effect transistors 200 and 202.

Thus, the first state of the chopper drive generates a voltage waveform which is square. However, the square voltage waveform is of insufficient peak-to-peak voltage to drive the chopper because of the voltage drop across the channel resistors 206 and 208.

Therefore, the succeeding or second stage of the chopper drive, which is AC coupled to the preceding stage through capacitors 217 and 219, comprises another or second pair of field effect transistors 216 and 218 which are biased near their respective threshold voltages by resistors 220, 222 and 224 which are connected to the gate electrodes thereof. By biasing the transistors 216 and 218 near their threshold voltages the transistors turn on very near the zero crossing of the square wave signal generated by the transistors 200 and 202. As a result, the duty factor of each of the transistors 216 and 218 more closely approaches 50% thereby eliminating any phase uncertainty so as to assure reliable phase detection at the chopper 44. Since the transistors 216 and 218 do not conduct simultaneously except for the instant of transition, there is little or no power wasted by the second stage.

Note that the transistors 216 and 218 are connected directly across the power supply voltage $+V_1$ and circuit common so that the output to the chopper 44 is alternately switched between $+V_1$ and circuit common. This produces a low output impedance in the chopper drive to assure fast rise and fall times of the resulting square wave output signal without the necessity of dissipating large amounts of power in the chopper drive. Accordingly, the square wave output signal generated by the field effect transistors 216 and 218 connected between the supply voltage $V_1$ and circuit common very closely approaches a perfect square wave so as to assure phase stability in the phase sensitive detection without sacrificing efficiency of the chopper drive.

Where a probe is utilized to measure the level of liquids and the liquids tend to coat the probe, it is desirable to provide means by which the phasing of the chopper drive square wave signal may be altered by a 45° lead. In this connection, it will be understood that long coatings on a probe as described in the aforesaid U.S. Pat. No. 3,706,980, which is incorporated herein by reference, appear as an infinite transmission line and the conductive and susceptive components of the coating are equal so as to produce a 45° lag. By detecting at a 45° phase angle, the conductive component and the susceptive component will cancel leaving only the susceptance due to the change in capacitance of the liquid level being measured and no susceptance due to the coating itself. In this connection, capacitor 226 and series resistor 234 or the capacitor 228 may be optionally connected in parallel with a capacitor 230.

Figure 4:
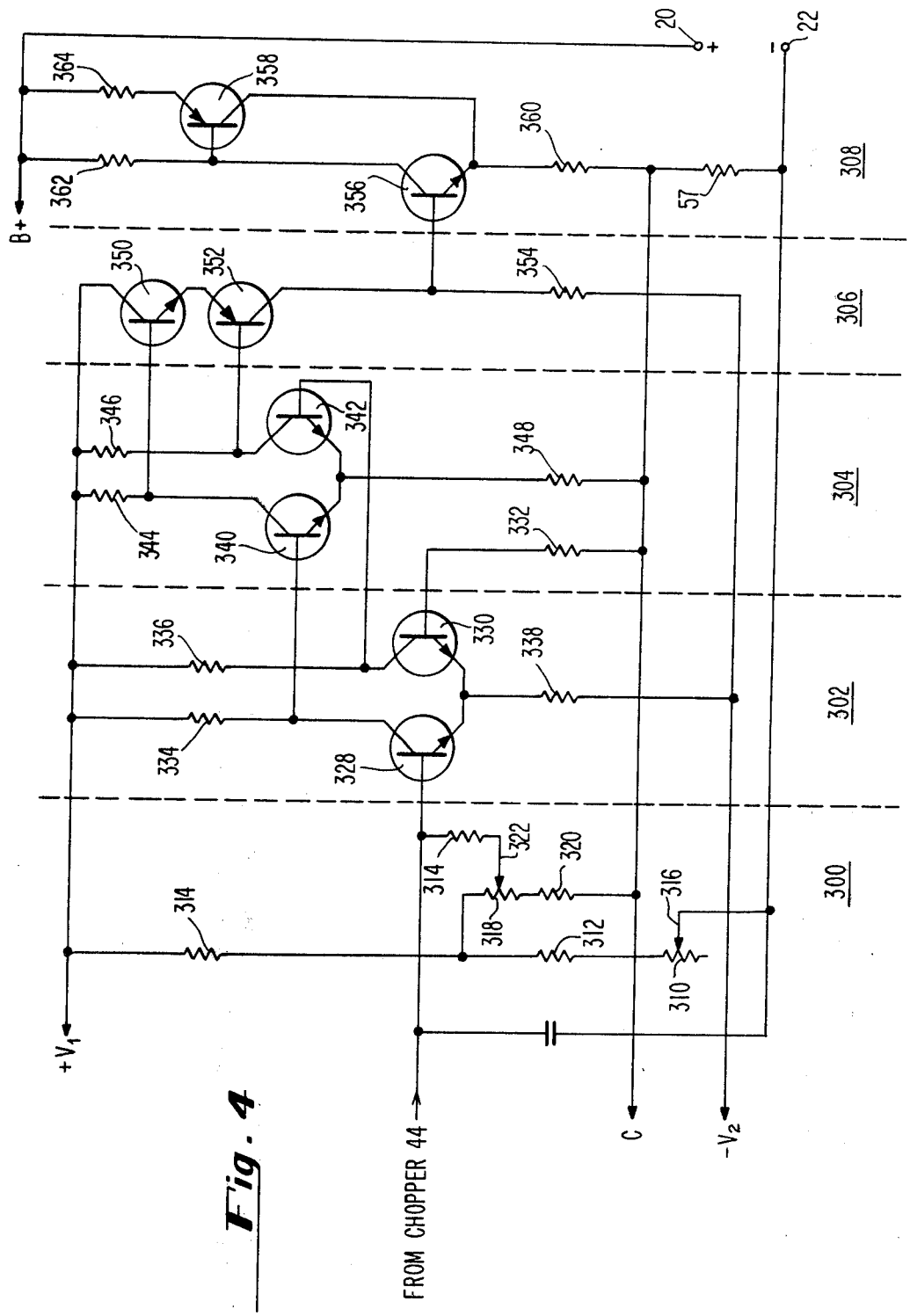
FIG. 4 is a schematic circuit digram of an output amplifier embodying another important aspect of the invention.

In accordance with another important aspect of the invention, the output amplifier 56 comprises a voltage feedback network connected to a resistor 57 as shown in FIG. 1 through which the 4-20 milliamp DC current drawn by the two-wire transmitter flows so as to stabilize the flow of the 4-20 milliamp DC current at all current levels. As shown in FIG. 4, the output amplifier 56 is divided into the following sections: a voltage feedback divider network 300, a first differential amplifier stage 302, a second differential stage 304, a voltage to current gain stage 306 and an output amplifier stage 308 which is shown as including the resistor 57 connected between circuit common and the terminal 22 in FIG. 1.

The voltage feedback divider network 300 includes an independent point adjustment potentiometer 310 connected in series with resistors 312 and 314. A tap 316 on the potentiometer 310 is set so that when the bridge network 26 shown in FIG. 1 is at balance, the current drawn by the two-wire transmitter is 4 milliamps when no current is flowing through the gain adjustment network comprising a potentiometer 318 in series with a resistor 320 and having a adjustable tap 322 connected to the input of the first differential stage 302 through a resistor 324. When there is no current flowing through the gain adjustment network, the voltage with respect to circuit common C at the tap 322 remains at zero volts throughout the entire range of gain control.

The differential amplifier stage 302 comprises a first transistor 326 having a base connected to the output from the chopper 44 and the voltage feedback network 300. The base of a second transistor 330 is connected to circuit common C through a resistor 332. The differential amplifier stage 302 includes biasing resistors 334, 336 and 338 which are connected between the positive power supply terminal $+V_1$ and the negative power supply terminal $-V_2$.

The second amplifier stage 304 comprises a first transistor 340 having a base connected to the collector of the transistor 328 and a second transistor 342 having a base connected to the collector of the transistor 330. Biasing resistors 344, 346 and 348 are connected between the positive power supply terminal $+V_1$ and circuit common.

The collectors of the transistors 340 and 342 are connected to the bases of a pair of transistors 350 and 352 of the voltage to current stage 306. The collector-emitter circuits of the transistors 350 and 352 are connected in series with a resistor 354 between the power supply terminal $+V_1$ and the negative power supply terminal $-V_2$.

The output stage comprises a pair of transistors 356 and 358 where the base of the transistor 356 is connected to the junction of the resistor 354 and the collector of the transistor 352 in the voltage to current gain stage 306. The output current from the output stage 308 is connected to the resistor 57 through a resistor 360. Resistors 362 and 364 connect the collector and emitter of the resistors 356 and 358 respectively to the terminal 20 of the two-wire transmitter.

When an unbalance is created at the bridge network 26, the voltage output from the chopper 44 increases which tends to make the base of the transistor 328 more positive. This renders the transistor 328 more conductive and the transistor 330 less conductive which in turn causes the voltage at the collector of the transistor 328 to decrease and the voltage of the collector of the transistor 330 to rise. The voltages at the collectors of the transistors 328 and 330 are then applied as input to the bases of the transistors 340 and 342 causing the voltages at the collectors of the transistors 340 and 342 to increase and decrease respectively. This in turn causes the transistors 350 and 352 to become more conductive and increase the current flow through the resistor 354 thereby raising the base of the transistor 356 to a more positive voltage causing an increase in current flow from the output transistors 356 and 358.

Since all of the current from the output transistors 356 and 358 flows through the resistor 57, the voltage across the resistor 357 will increase with increasing current flow due to the unbalance of the bridge network thereby decreasing the voltage at the terminal 22 with respect to circuit common C. This is turn increases the negative voltage which is applied to the base of the transistor 328 through the voltage feedback divider network until that voltage is again zero volts thereby establishing a stable condition at the higher output current.

From the foregoing, it should be understood that the output amplifier 56 may be analogized to an operational amplifier having one input at the base of transistor 328 acting as a summing junction for the voltage from the output of the chopper 44 and the voltage of the voltage feedback divider network 300 and the other input at the base of the transistor connected to circuit common.

In accordance with another important aspect of the invention, the length of the cables associated with the probe will not affect the admittance measurements.

Figure 5:
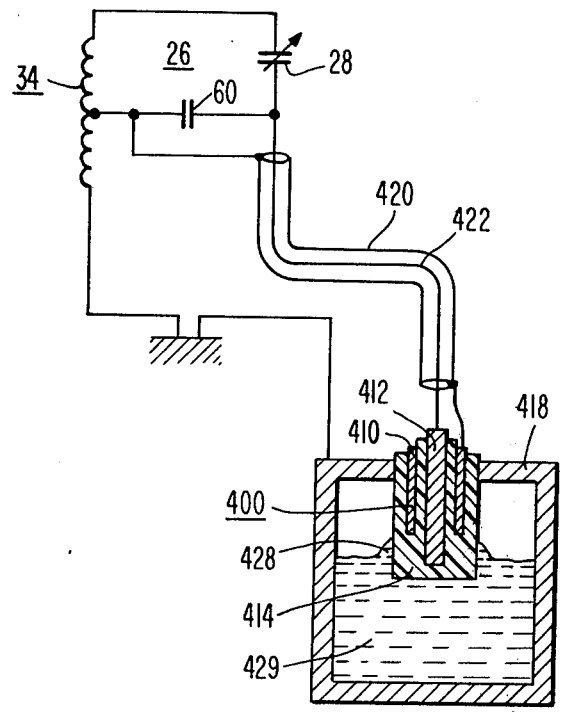
FIG. 5 is a schematic representation of the bridge network including a mechanical representation of the probe.

As shown in FIG. 5, a probe 400 is connected into the bridge network 26. The probe 400 includes a guard electrode 410 juxtaposed to and surrounding a probe electrode 412. Insulation 414 surrounds the probe electrode 412 so as to insulate the guard electrode 410 from the probe electrode 412 and the guard electrode 410 from a grounded conductive vessel 418. A coaxial cable is utilized to connect the probe 400 into the bridge network 402 where the shield of the cable 420 is connected to the guard electrode 410 at one terminal of the span capacitor 60 and the axial conductor 422 connects the probe electrode 412 to the other terminal of the span capacitor 60.

Figure 6:
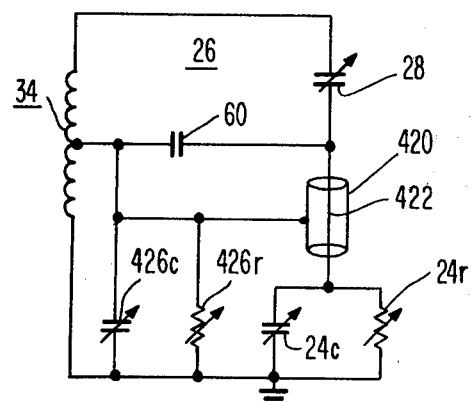
FIG. 6 is an equivalent circuit of the bridge network of FIG. 5.

Reference to FIG. 6, wherein the equivalent circuit of FIG. 5 is shown, reveals that a variation in the cable length will have no effect on the admittance measurement. As shown, the probe electrode to ground admittance 24 is represented by a capacitance 24c and a resistance 24r. Since the axial conductor 422 is surrounded by the coaxial shield 420 which is connected to the opposite terminal of the span capacitance 60, any admittance between the coaxial shield 420 and the axial conductor 422 will be connected across the span capacitance 60 and will not affect the balance or unbalance of the bridge network. Similarly, any admittance between the coaxial shield 420 and ground as represented by a capacitance 426c and a resistance 426r will have no effect on the balance of the bridge network 26 since this admittance is in parallel with the secondary 24 of the transformer.

In accordance with another important aspect of the invention, linear calibration of the admittance measuring system is achieved by making the span capacitance 60 large relative to the capacitance of the admittance being measured as disclosed in U.S. Pat. No. 3,778,705 - Maltby. Preferably, the capacitance of the span capacitor 408 or the span capacitor 26 is at least 10 times the capacitance of capacitance 424c or capacitance 24c. In a particularly preferred embodiment, the span capacitance is 25 times the capacitance being measured.

As shown in FIG. 5, the probe 400 comprises a probe electrode 412 which is completely surrounded with insulation 414. As also shown, the insulation 414 is coated with materials 428 contained within the vessel 418. As will now be explained, the probe electrode-to-ground resistance 24r will, in substantially all applications, be in excess of the previously mentioned 500 ohms even when the probe is covered with a coating 428 of conductive liquid 429 as shown in FIG. 5.

Figure 7A:
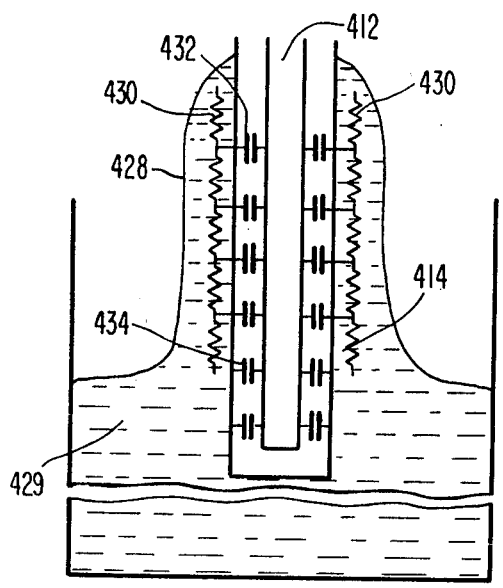
FIGS. 7(a-c) are schematic representations of various probes immersed in various materials.
Figure 8A:
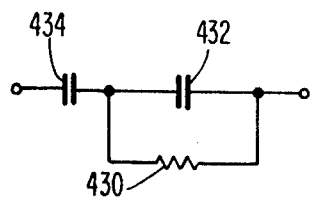
FIGS. 8(a-c) are equivalent circuits of the admittance measured by the probes of FIGS. 7(a-c) respectively.
Figure 9:
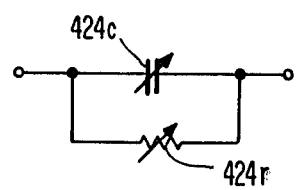
FIG. 9 is an equivalent circuit of the admittance of FIGS. 8(a-c)

Referring now to FIG. 7a, a schematic representation of the coating 428 on the probe 400 of FIG. 5 illustrates the nature of the probe-to-ground resistance. As shown there, the coating 428 may be represented by a series of small resistors 430 which are coextensive with the length of the coating. The junction of these resistors 430 are connected to the probe electrode 414 by shunt capacitors 432 which represent the capacitance of the insulation 414. An equivalent circuit corresponding to the probe and coating of FIG. 7a is illustrated in FIG. 8a wherein the capacitor 432 is connected in shunt with the resistor 430. A capacitor 434 represents the capacitance through the insulation 414 from the conductive liquid below the coating 428 to the probe electrode 412. This equivalent circuit may in turn be represented as shown in FIG. 9 by the shunt resistor 424r and the shunt capacitor 424c. It has been found that in substantially all applications where the resistance 424r as shown in FIG. 9 is contributed by the coating 428 as represented by the series of resistors 430 shown in FIG. 7a, the resistance 424r is more than 500 ohms.

Figure 7B:
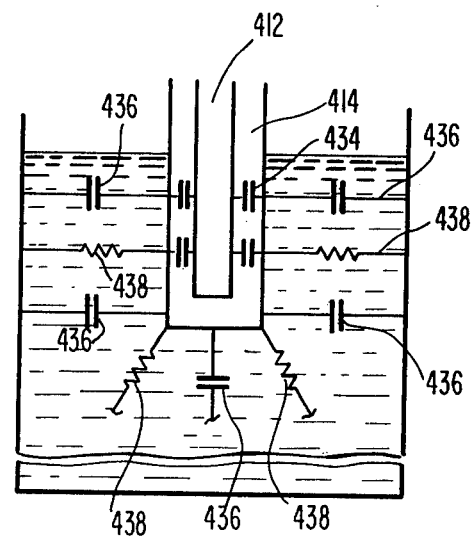
Figure 8B:
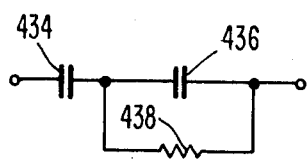

FIG. 7b represents the insulated probe 400 of FIG. 5 immersed in a semi-conductive liquid wherein the liquid itself is represented by a number of shunt capacitors 436 and shunt resistors 438. The equivalent circuit for the immersed probe of FIG. 7b is shown in FIG. 8b wherein the shunt capacitors 436 and the shunt resistors 438 are connected in parallel and a capacitor 434 again represents the capacitance through the insulation from the materials to the probe electrode 412. The equivalent circuit of FIG. 8b may of course also be depicted as a shunt resistor-capacitor combination as shown in FIG. 9. Although the resistor 438 is now contributed by the semi-conductive material rather than the coating as in the immersed probe of FIG. 7a, it has nevertheless been found that the equivalent resistance 424r as depicted in FIG. 9 will, in substantially all cases, exceed 500 ohms for the immersed probe of FIG. 7b.

Figure 7C:
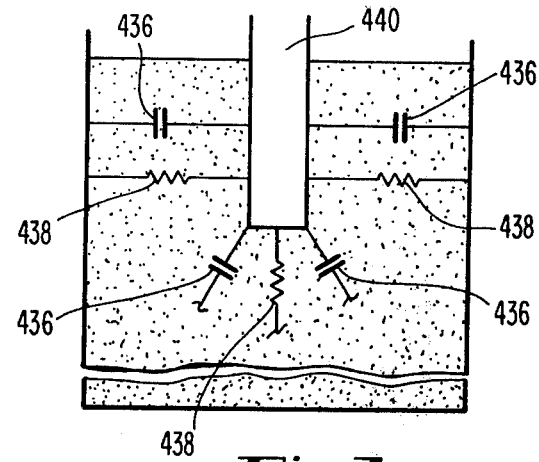
Figure 8C:
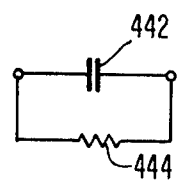

Finally, FIG. 7c depicts a bare probe 440 immersed in semi-conductive materials which may be represented by shunt capacitors 436 and shunt resistors 438 which are depicted in schematic circuit form by a resistance 442 and a resistance 444 in FIG. 8c. Once again, it has been found that the resistance 444 which represents the resistance 424r of FIG. 9 in the bridge network will exceed 500 ohms for almost all applications.

As described in the foregoing, the invention may be utilized with insulated as well as bare immersions probes including guard electrodes of the type described in Maltby U.S. Pat. No. 3,879,644 and incorporated herein by reference. It will of course be appreciated that the invention is equally applicable to two terminal probes without a guard electrode. It will also be understood that the invention is applicable to non-linear probes wherein the probe electrode is characterized, i.e., the cross-sectional dimension of the probe electrode varies from one end of the probe electrode to the other. Probes of this type are disclosed in Schreiber U.S. Pat. No. 3,269,180 which discloses a non-linear probe without a guard electrode and a non-linear probe with a guard electrode as disclosed in copending application Ser. No. 532,208 filed Dec. 12, 1974 assigned to the assignee of this invention, both of which are incorporated herein by reference. Furthermore, the invention is applicable to non-immersible probes which sense the condition of an admittance material when in close proximity therewith.

In the foregoing, the invention has been described in terms of a two-wire transmitter. It will of course be appreciated that many aspects of the invention may be embodied in other applications such as, for example a battery powered system, wherein the power available is as limited if not more limited than the two-wire transmitter application.

Figure 10:
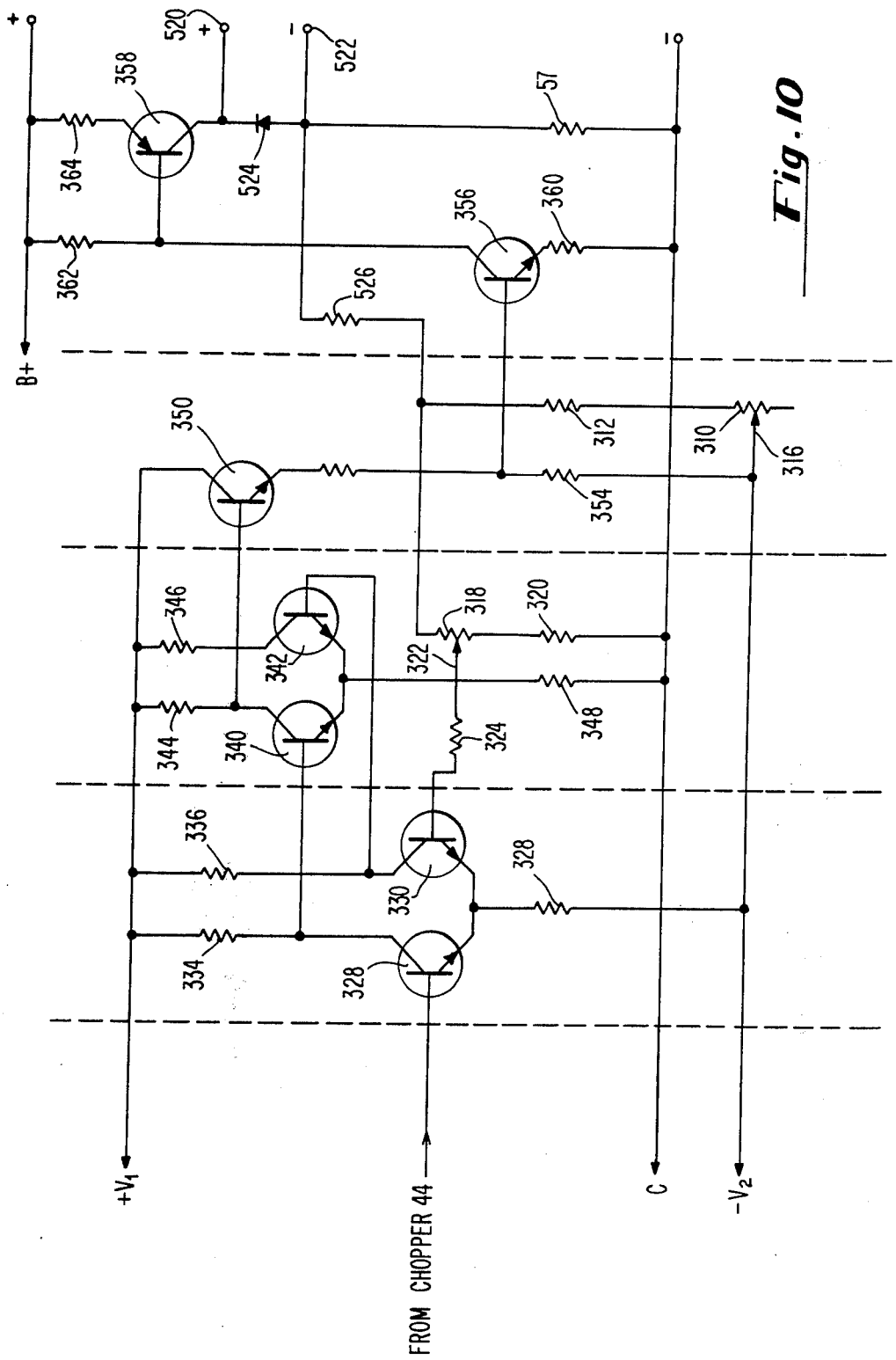
FIG. 10 is a schematic diagram of a battery-powered output amplifier.

In this connection, another output amplifier 56 for use in a battery powered system will now be described with reference to FIG. 10. As shown there, the output amplifier is in many respects similar to the output amplifier shown in FIG. 4 and substantially identical circuit elements bear identical reference characters.

However, the output amplifier of FIG. 9 differs in that the voltage feedback from the resistor 57 is not applied to a summing junction in the first differential amplifier stage but rather to the other input of the differential amplifier at the base of the transistor 330. The output signal is represented by the current flow to and from output terminals 520 and 522 at the terminals of a diode 524 in the collector-emitter circuit of the transistor 358.

In operation, a positive input at the base of the transistor 328 and a first differential amplifier stage tends to increase the current flow through the resistor 57. This in turn raises the positive voltage applied to the base of the transistor 330 of the voltage divider network comprising the resistors 310, 312 and a resistor 526. As a result, the current through the resistor 57 and the output current terminals 520 and 522 is stabilized at a higher current level.

It should be understood that the output amplifier described is in effect an operational amplifier having one input connected to the output of the chopper and the other input connected to a voltage feedback network as contrasted with the circuit of FIG. 4 wherein one input served as a summing junction connected to the chopper output as well as the voltage feedback network and the other input was connected to circuit common.

Although the chopper 44 has not been shown in detail, it will be understood that the chopper circuits and output amplifier circuits well known in the art are suitable for use in the two-wire transmitter system of this invention. For example, the chopper circuit disclosed in the aforesaid Schreiber U.S. Pat. No. 3,778,705 may be utilized. The output amplifier may comprise any of a number of commercially available differential amplifiers. It will also be understood that various resonant circuits may be utilized to replace the tank circuit shown in FIG. 1. Similarly, the voltage regulator circuit 58 may comprise a prior art voltage regulator well known in the art.

Another embodiment of the invention will now be described with reference to FIG. 11. As shown therein, terminals 20 and 22 of the two-wire transmitter are connected to the full wave rectifying bridge comprising diodes 70, 72, 74 and 76 as described in conjunction with the embodiment of FIG. 1. As in the previously described embodiment, the diodes of the full wave rectifying bridge permit the polarity of the terminals 20 and 22 to be reversed without risk of damaging the transmitter or affecting the operation thereof. A spark protection Zener diode 502 is connected across the full wave rectifying bridge so as to limit the voltage which can be applied to the signal processing circuitry The output from the full wave rectifying bridge is connected to a voltage regulator 500 which supplies substantially constant voltages for various components of the transmitter thereby avoiding any inaccuracies in measurements due to undesirable variations in the supply voltage of the transmitter.

In accordance with this embodiment of the invention, the admittance responsive network comprises a probe oscillator 504 having a frequency which is determined by the probe-to-ground admittance of the materials being sensed as coupled into the probe oscillator 504 through a transformer 506. The frequency of the probe oscillator 504 is then compared at a frequency difference detector 507 with the frequency generated by a reference oscillator 508 having a frequency determined by a reference admittance including zero step capacitors 510 (shown as a single variable capacitor) and a fine zero capacitor 512 which are coupled to the reference oscillator 508 through a transformer 514.

In accordance with one important feature of this embodiment, a compensate terminal is provided between the junction of the fine zero capacitor 512 and the step zero capacitor 510. This allows the use of matched cable sets which may be connected to the probe terminal and the compensate terminal to eliminate the effect in varations in cable parameters on the measurements of the two-wire transmitter.

Figure 11:
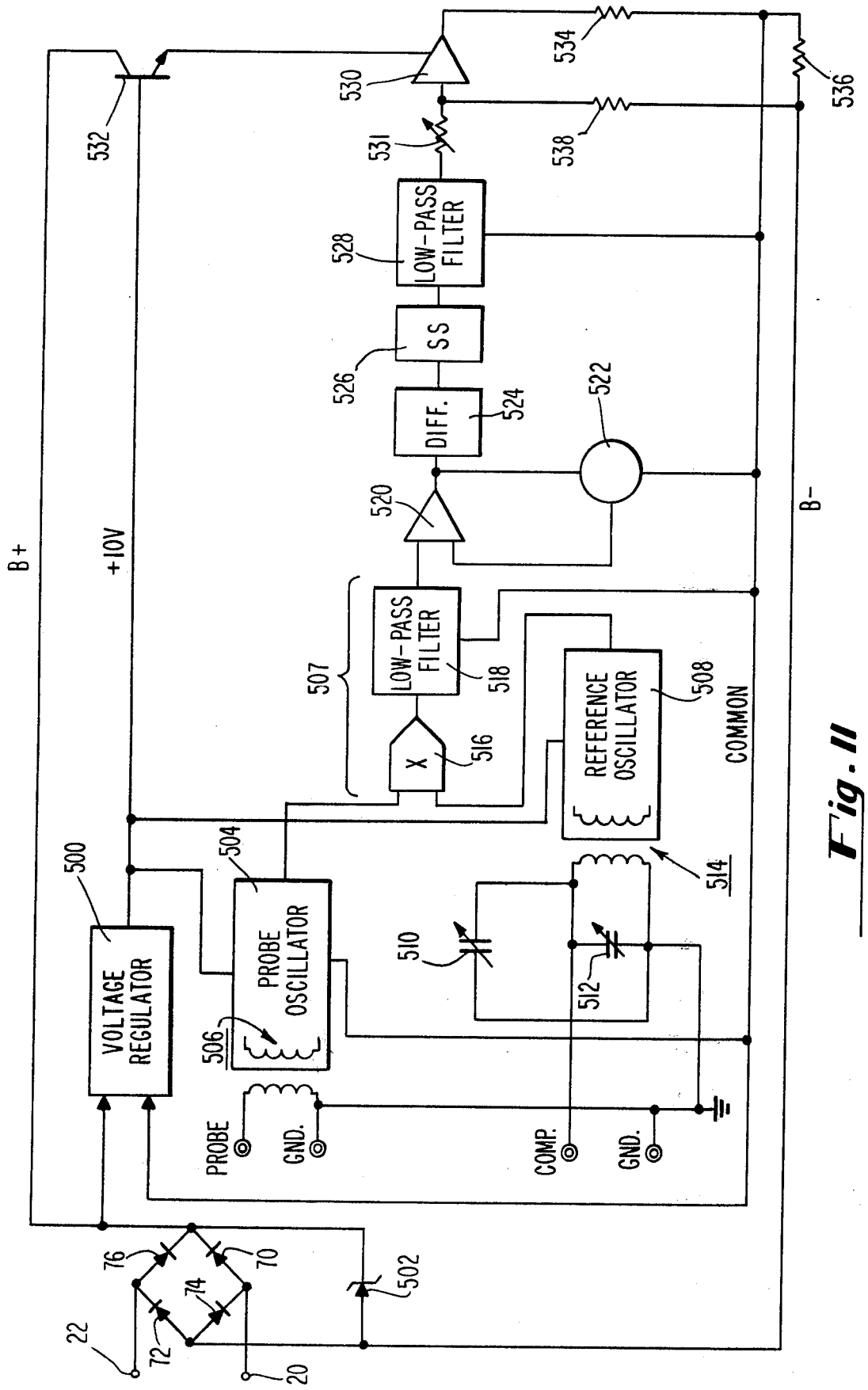
FIG. 11 is a block diagram of another two-wire transmitter representing an embodiment of the invention.

As shown in FIG. 11, the probe-to-ground admittance coupled into the probe oscillator 504 and the reference admittance coupled into the reference oscillator 508 form two sides or halves of an admittance bridge. In effect, the bridge unbalance resulting from changes in the probe-to-ground admittance is measured by measuring the difference in frequency between the oscillators 504 and 508 at the frequency difference detector 507. The frequency different detector 507 includes a multiplier 516 which is coupled to a low pass filter 518 so as to generate a signal representing the difference between the input frequencies of the probe oscillator 504 and the reference oscillator 508.

The output from the low pass filter 518 which represents the frequency difference is applied to a squaring amplifier 520 having a feedback path 522 so as to establish hysteresis which is substantially less than the amplitude of the frequency difference signal and substantially larger than the amplitude of the carrier frequency components. The output of the amplifier 520 will be a square wave whose frequency is the difference between the frequencies of the probe oscillator 504 and the reference oscillator 508. A differentiating network 524 is coupled to the output of the squaring amplifier 520 so as to generate pulses having a frequency proportional to the frequency difference between the probe oscillator 504 and the reference oscillator 508 which are in turn coupled to a one-shot multivibrator 526. The output from the one-shot multivibrator 526 is a train of pulses of constant width and having a pulse repetition rate equal to the difference in frequencies between the probe oscillator 504 and the reference oscillator 508. Accordingly, the average DC value of the pulse train from the multivibrator 526 is proportional to its duty factor and this average value is determined by a low pass filter 528 which is coupled to an output amplifier 530 through a fine span potentiometer 531. The output from the amplifier 530 controls the amount of current drawn through a transistor 532 and a resistor 534 connected in series with a resistor 536. As the current drawn through the resistor 536 changes, the feedback voltage applied to the output amplifier 530 through a resistor 538 varies so as to provide closed-loop control of the current flowing through the resistor 536 which in turn substantially represents the total current drawn by the instrument.

Figure 12A:
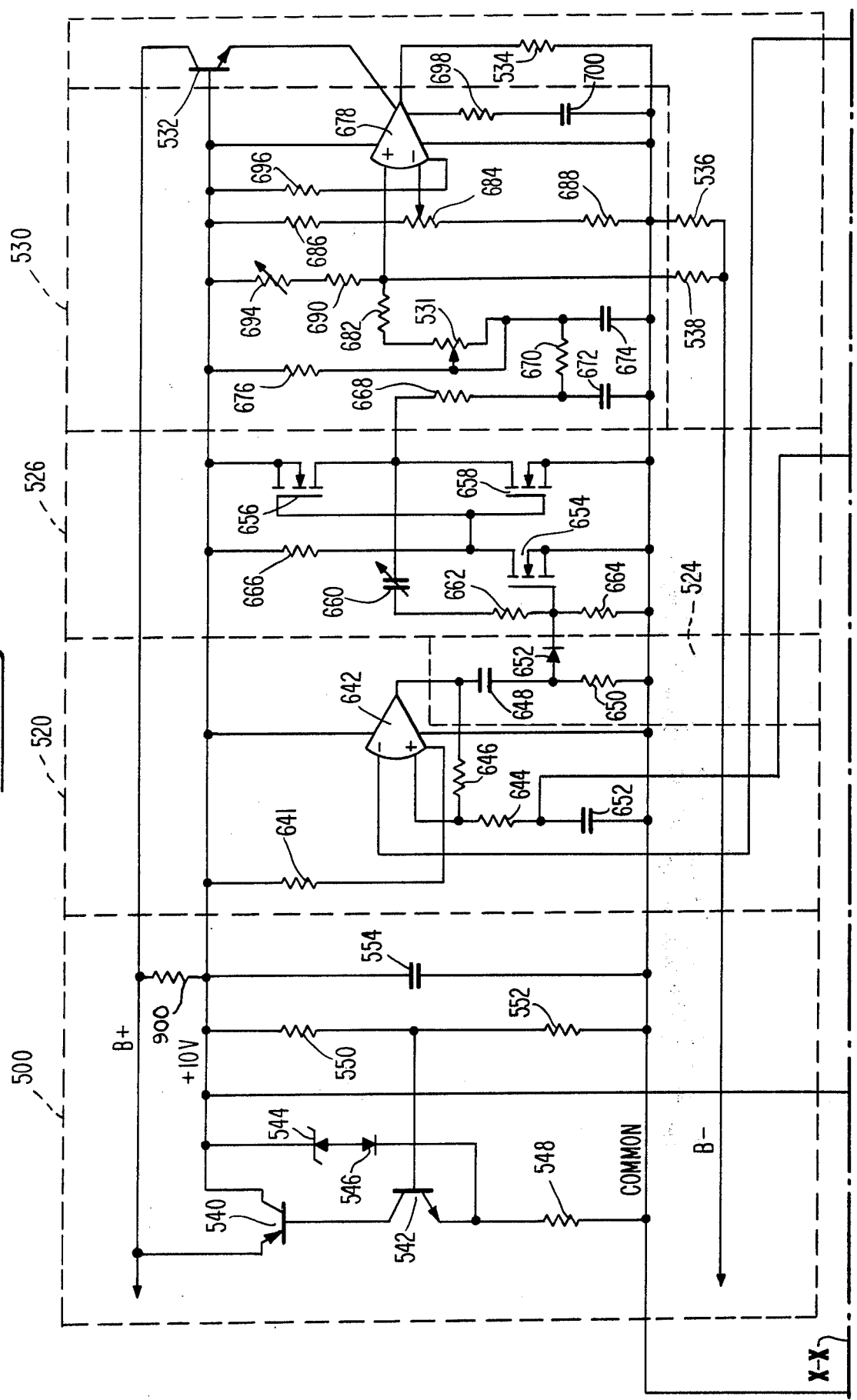
FIG. 12 is a schematic diagram of circuitry shown in block form in FIG. 11.

Reference will now be made to the detailed circuitry shown in FIGS. 12a and 12b. As shown in FIG. 12a, the voltage regulator 500 comprises transistors 540 and 542. The collector of the transistor 540 establishes a +10 volt regulated supply where the collector of the transistor 540 is connected to the emitter of the transistor 542 through a temperature compensating diode 544 in series with a reverse poled diode 546. The emitter of the transistor 542 is connected to regulated circuit common through a resistor 548 and resistors 550 and 552 establish a bias for the base of the transistor 542. A capacitor 554 acts as a filter for the voltage regulator. In addition, the voltage regulator 500 comprises a start-up resistor 900 between the B+ line and the +10 volt line.

Figure 12B:
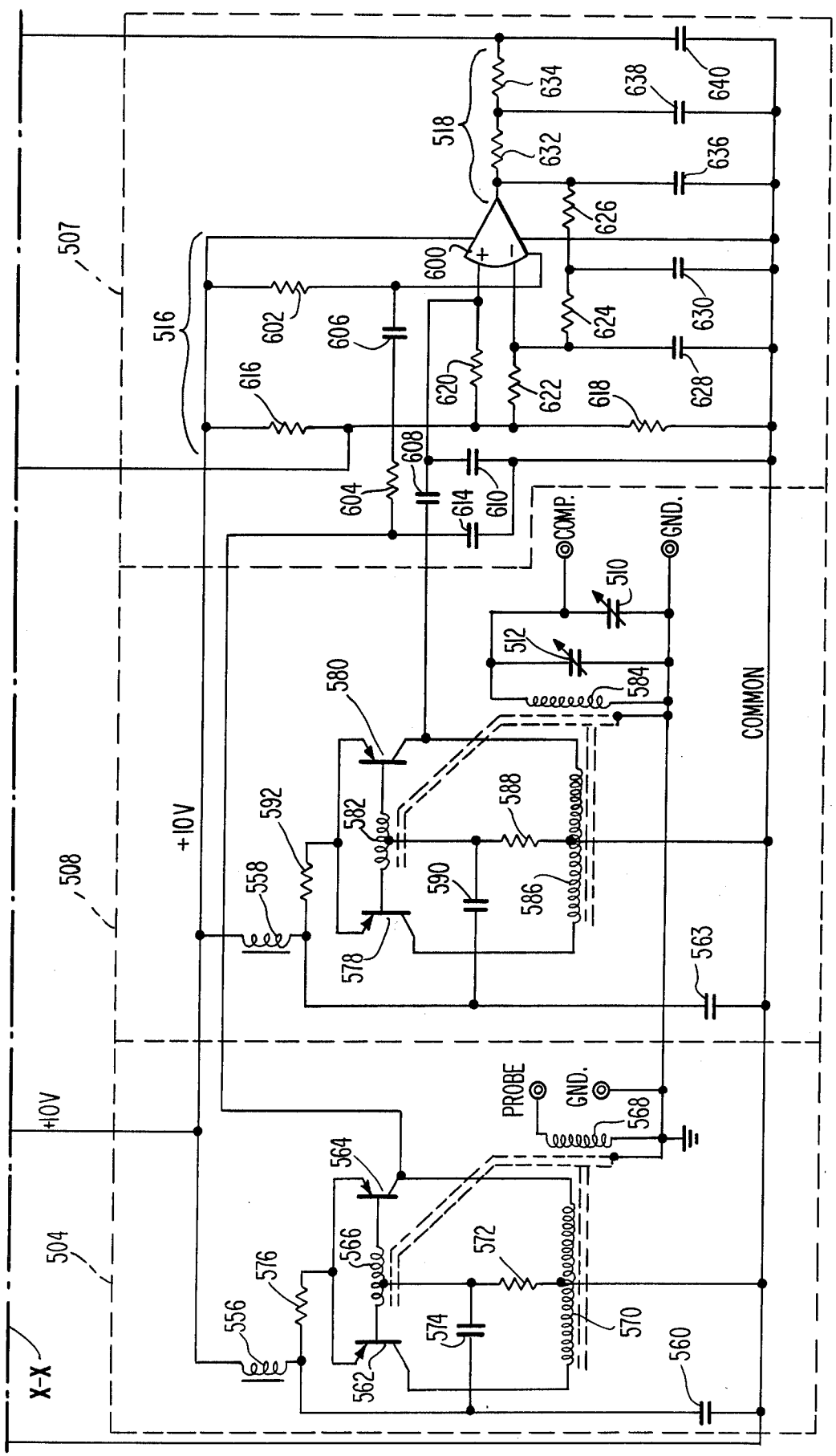

The +10 volt common terminals of the voltage regulator are connected to the probe oscillator 504 and the reference oscillator 508 shown in FIG. 12b. Both the probe oscillator 504 and the reference oscillator 508 are of the Class C type for high efficiency and are respectively decoupled by choke coils 556 and 558 and capacitors 560 and 563. A pair of probe oscillator transistors 562 and 564 have bases interconnected by a winding 566 which is transformer coupled to a winding 568 connected between probe and ground, and the winding 568 is also coupled to a winding 570 which connects the collectors of the transistors 562 and 564. A resistor 572 connects center taps of the windings 566 and 570.

If the oscillator 504 is not running, current flow through the resistor 572 will bias the transistors into the linear region. When the oscillator begins running, base rectification in the transistors 562 and 564 charges the capacitor 574 connected between the center tap of the winding 566 and the junction of the capacitor 560 and the coil 556 resulting in a very efficient Class C mode of operation. A resistor 576 connects the junction of the coil 556 and the capacitor 560 to the emitters of the transistors 562 and 564 so as to reduce the amplitude of the resulting current pulses and spread their width thereby reducing the harmonic distortion present in the output waveform.

The reference oscillator 508 includes components which are comparable to those of the oscillator 504. In particular, the oscillator 508 includes transistors 578 and 580 having bases interconnected by a winding 582 coupled to a winding 584 connected between the compensate terminal and ground. The collectors of the transistors 578 and 580 are connected by another winding 586 with the center taps of the windings 582 and 586 being connected by a resistor 588. The reference oscillator 508 is also capable of Class C operation provided by the charging of the capacitor 590 which holds the transistors 578 and 580 off during most of the cycle. A resistor 592 connected between the emitters of the transistors 578 and 580 at the junction of the coil 588 and the capacitor 563 reduces the amplitude of the current pulses and spreads their width as in the case of the resistor 576 in the probe oscillator 504.

In practice, the voltage appearing across the winding 570 and the winding 586 will be approximately 40 volts peak-to-peak with each end going plus and minus 10 volts. The base-to-base voltages of the transistors 562 and 564 and the transistors 578 and 580 will be driven at 4 volts peak-to-peak, and since each base will be driven at 2 volts peak-to-peak, the center tap of the windings 566 and 582 will be approximately 1 volt positive with respect to the base of the conducting transistor or about 0.3 volts positive with respect to the emitter.

The time constant of the resistor 572 and the capacitor 574 and the time constant of the resistor 588 and the capacitor 590 are chosen so as to permit the capacitors to discharge approximately 0.1 volts in each half cycle. This assures that there will be a pulse in the following half cycle if the Q of the tank circuit is at least 5. It is necessary that every half cycle have a current pulse in order to prevent squegging or envelope modulation of the oscillators output waveform.

It will therefore be understood that the probe oscillator 504 and the reference oscillator 508 are substantially identical. However, the probe oscillator includes the probe admittance in the tank circuit whereas the reference oscillator includes the compensate admittance between the compensate terminal and ground, a fine zero capacitance 512 and a step zero capacitance 510. Moreover, the admittance of the probe oscillator and the reference oscillator forms a bridge where the ratio of the inductance of the winding 568 to the inductance of the winding 584 is equal, at bridge balance, to the ratio of the combined fine zero capacitance 512, step zero capacitance 510 and the capacitive part of the compensating admittance to the capacitive part of the probe admittance at bridge balance.

As the bridge moves off balance, the frequency of the probe oscillator 504 will change producing a difference in frequency between the reference oscillator and the probe oscillator. The voltages produced by these oscillators are applied to the multiplier 516 of the frequency difference detector. Depending upon the balance of this multiplier circuit, components may appear in the output proportional to each of the input frequencies, the sum of the input frequencies, and the difference between the input frequencies. Of these, the difference between the input frequencies will be of a much lower frequency than any of the others. Thus, the difference frequency can be filtered off by a simple low pass filter network. As shown in FIG. 12b, the multiplier comprises a programmable amplifier 600 such as the RCA CA3080. The bias current for the amplifier is provided by resistors 602 and 604 and a capacitor 606. These components are arranged so that the peak value of the component due to the probe oscillator 504, through the resistor 604 and the capacitor 606, is approximately equal to the DC value from +10 volts through the resistor 602. A capacitor divider comprising capacitors 608 and 610 place a small fraction of the voltage of the output of the reference oscillator 508 on the positive input of the amplifier 600 whose negative input is maintained at AC common by a capacitor 628. The DC operating point of the amplifier 600 is determined by resistors 616, 618, 620 and 622. A capacitor 614 which is connected across the transformer of the probe oscillator 504 is equal to the total capacitance represented by capacitors 608 and 610 connected across the transformer of the reference oscillator 508.

A low pass filter comprising resistors 624 and 626 and capacitors 628 and 630 is connected to circuit common so as to provide a very low frequency cutoff filter stabiize the DC operating point of the amplifier 600 at the voltage appearing at the junction of the resistors 616 and 618. Resistors 632 and 634 and capacitors 636, 638 and 640 form a low pass filter 518 whose cutoff frequency lies between the highest output frequency desired, and the operating frequency of the probe oscillator 504 and the reference oscillator 508. The low pass filter 518 in conjunction with circuitry of the squaring amplifier 520 provides an AC signal at the difference frequency which is amplified by the squaring amplifier 520 without transmitting a significant amount of carrier frequency.

The squaring amplifier 520 will now be described in somewhat more detail with reference to FIG. 12a. The output voltage of the low pass filter 518 is applied to the inverting or negative input terminal of an operational amplifier 642 of the squaring amplifier 520. A reference voltage is applied to the non-inverting or positive input of the operational amplifier 642 which is coupled to the junction of the resistors 616 and 618 in the frequency difference detector 506 through a resistor 644. The resistor 644 connected to ground through a capacitor 652 in conjunction with another resistor 646 forms a divider network which feeds back a small fraction of the output voltage of the operational amplifier 642 to provide hysteresis. The hysteresis of the squaring amplifier is substantially less than the amplitude of the frequency difference signal and substantially larger than the amplitude of the carrier frequency components. Thus, the output of the amplifier 642 will be a square wave whose frequency is the difference between the frequencies of the reference oscillator 508 and the probe oscillator 504. The output from the operational amplifier 642 is coupled to the differentiating circuit 524 comprising a capacitor 648 and a resistor 650. The output from the differentiating circuit 524 is connected to the one-shot multivibrator 526 through a diode 652.

As shown in FIG. 12a, the one-shot multivibrator 526 comprises field effect transistors 654, 656, and 658. A positive pulse coupled through the diode 652 to the gate of the transistor 654 enhances it, driving the gates of the transistors 656 and 658 negative. This causes the positive transistor 656 to be enhanced, providing a positive output. At the same time, a step span capacitance 660 (shown as a variable capacitor for simplicity) is selected by a switch and raises the voltage on the gate of the transistor 654 to a high level, e.g., approximately 10 volts. As the step span capacitance charges through resistors 662 and 664, the voltage at the gate of the transistor 654 decays exponentially until it reaches the threshold voltage of the transistor 654. At that time, the transistor 654 turns off and the transistors 656 and 658 receive a positive gate voltage causing the output to return negative. The selected capacitor drives the gate of the transistor 654 hard negative, but the current supplied to the gate protection diodes is limited by the resistor 662 to prevent the capacitor discharge from damaging the gate metalization. By making the resistor 662 considerably smaller than the resistor 664, the one-shot multivibrator is ready for another pulse in a small fraction of its operating time.

The time constant provided by the step span capacitor 660 and the resistors 662 and 664 is such as to permit the one-shot multivibrator to have a duty factor in the range of 80–90% at the full-scale output. The output of the multivibrator 526 is a pulse train, whose pulses have a constant width determined by the step span capacitor 660 at a pulse repetition rate equal to the difference in frequencies between the probe oscillator 504 and the reference oscillator 508. The average DC value of this pulse train is directly proportional to its duty factor, which is in turn directly proportional to the pulse repetition rate since the pulses are of constant width, and thus, to the difference in frequency between the probe oscillator 504 and the reference oscillator 508.

The output from the multivibrator 526 is applied to the output amplifier 530 which will now be described in detail with reference to FIG. 12a. The DC value from the multivibrator 526 is filtered off by resistors 668 and 670, and capacitors 672 and 674 at the input of the output amplifier 530. A resistor 676 connected in series with the resistors 668 and 670 raises the voltage at the junction of the resistor 670 and the resistor 676 to a value within the operating range of the operational amplifier 678. The junction of the resistor 670 and the resistor 676 is connected to the positive terminal of an operational amplifier 678 through a fine span potentiometer 680 in series with a resistor 682. A balance potentiometer 684 connected in series between resistors 686 and 688 is used to adjust the negative input of the operational amplifier 678 to be the same as the voltage at the junction of the resistor 682 and resistors 690 and 538 when there is no pulse train coming from the multivibrator 526. As a result, there is no voltage across the fine span potentiometer 680 at balance, and thus, the current drawn by the instrument is independent of fine span setting. A poteniometer 694 is connected in series with the resistor 690 for adjusting the current flow. This current flow may be adjusted so as to establish 4 milliamperes in a 4–20 miliampere instrument when there is no pulse train from the multivibrator. In the alternative, another current may be established in a different current range.

As mentioned previously, substantially all of the current drawn by the instrument flows through the resistor 536 so as to generate a voltage relative to common which is proportional to the total current drawn by the instrument. This voltage is fed back through the resistor 538 to the positive input of the operational amplifier 678. The operational amplifier 678 responds to a positive input by increasing the current drawn through the resistor 534 and the transistor 532 thereby increasing the total current drawn by the instrument until the voltage drop across the resistor 536 brings the voltage at the positive input to the operational amplifier 678 down to the voltage at the negative input, thus giving closed-loop control of the total current drawn by the instrument.

A two-wire transmitter embodiment is shown in FIG. 11 and FIGS. 12a and 12b. However, the invention may be embodied in a battery powered application where the squared pulses from the output of the squaring amplifier 520 are counted or otherwise integrated and displayed.

A further embodiment of the invention will now be described with reference to FIG. 13. As shown therein, terminals 20 and 22 of the two-wire transmitter are connected to the full wave rectifying bridge comprising diodes 70, 72, 74 and 76 as described in conjunction with the embodiment of FIG. 1 as well as the embodiment of FIGS. 11, 12a and 12b. As in the previously described embodiments, the diodes of the full wave rectifying bridge permit the polarity of the terminals 20 and 22 to be reversed without risk of damaging the transmitter or affecting the operation thereof. The spark protection Zener diode 502 is connected across the full wave rectifying bridge so as to limit the voltage which can be applied to the signal processing circuitry. The output from the full wave rectifying bridge is connected to the voltage regulator 500.

In accordance with this invention, the admittance responsive network comprises a ramp-type admittance bridge. One side or half 790 of the bridge comprises a current source including a fixed zero current source 800 and a span current source 802 where resistance is included in the zero and span current sources. Both the zero current source and span current source are connected to the unknown admittance which is in series with a capacitor 803. The zero current source establishes a reference value of the unknown admittance while the span current source, having a magnitude controlled by an internallly generated feedback voltage so as to rebalance the bridge, establishes the full scale range of the bridge. The reference side or half 792 of the bridge comprises a resistance 804 in series with a capacitor 806.

The time required for the current sources 800 and 802 to change the voltage across the unknown admittance between probe and ground in ramp-like fashion is compared to the same time required for the reference resistance 804 to change the voltage across the reference capacitor by a fixed amount in the following manner. A reset circuit 808 including a comparator 810 is connected across the capacitor 803 and the probe-to-ground admittance. As shown in FIG. 13, the positive input to the comparator 810 is connected to the junction of the capacitor 803 and the current sources 800 and 802. The negative input to the comparator 810 is connected to a reference voltage 812. With switches 814 and 816 in the position shown, the unknown admittance from probe-to-ground and the capacitor 803 are free to charge in ramp-like fashion in response to current flow from the sources 800 and 802.

Simultaneously, a comparator 818 of the time difference detector circuit 820 compares the voltage across the reference capacitor 806 with a reference voltage 822. With a switch 824 of the reset circuit 808 in the position shown, the capacitor 806 is free to charge. By providing the reference resistor 804 and the reference comparator 806 with a shorter time constant than the time constant associated with the capacitor 803, the probe-to-ground admittance and the resistance associated therewith, the comparator 818 will produce a change in state of this output before the comparator 810 produces a change in the state of its output. When the positive input to the comparator 810 rises to a sufficiently high level, the state of the output from the comparator 810 will change which in turn changes the state of the switches 814, 816 and 824 to the opposite positions. When the switch 816 is in the opposite position, a reset voltage is applied to the negative input of the comparator 810. During the reset period, the voltage across the probe-to-ground capacitance and the voltage across the reference capacitor 806 diminish until such time as the voltage applied to the positive input of the comparator 810 falls below the reset voltage reference $V_{RS}$. At that time, the switches 814, 816 and 824 revert to the position shown and a new charging cycle is initiated. Upon reset, the output from the comparator 818 changes state so as to produce a pulse output representing the magnitude of the unknown admittance from probe to ground. In other words, the pulse width of the square wave represents the time difference in charging of the reference capacitor 806 vis a vis the probe-to-ground admittance.

The square wave output from the comparator 818 which is generated by switch means 826 is applied to a low pass filter 828 to obtain an average DC voltage at the output of the filter which is proportional to the difference in charge rate of the probe-to-ground admittance relative to the reference admittance 806. The output from the low pass filter 828 is applied to an amplifier 830 which produces a feedback voltage for controlling the span current source 802.

The output from the time difference detector 820 is then applied to a modulator 832. In accordance with one important aspect of the invention, the modulator 832 which is directly connected to the probe circuitry is isolated from the remainder of the transmitter circuitry by an isolating transformer 834 comprising a primary 836 and a secondary 838. Modulation is achieved by chopping the DC output from the amplifier 830 in response to the output from an oscillator 840. The chopping circuitry of the modulator 832 is depicted as an amplifier 842 in combination with switch means 844.

The oscillator 840 comprises a square wave oscillator section 846 which is directly connected to the voltage regulator 500 and an isolated supply section 848 which is coupled to the square wave oscillator 846 by an isolating transformer 850. The secondary of the isolating transformer 850 of the isolated supply 848 provides the chopper drive for the modulator 832. The isolated supply section 848 also provides a +11 and +5 volt supply to that portion of the two-wire transmitter circuitry which is connected directly to the probe and ground. The remainder of the transmitter circuitry including a demodulator 852 and an output circuit 854 are supplied by a +10 volt output from the voltage regulator 500.

Figure 13:
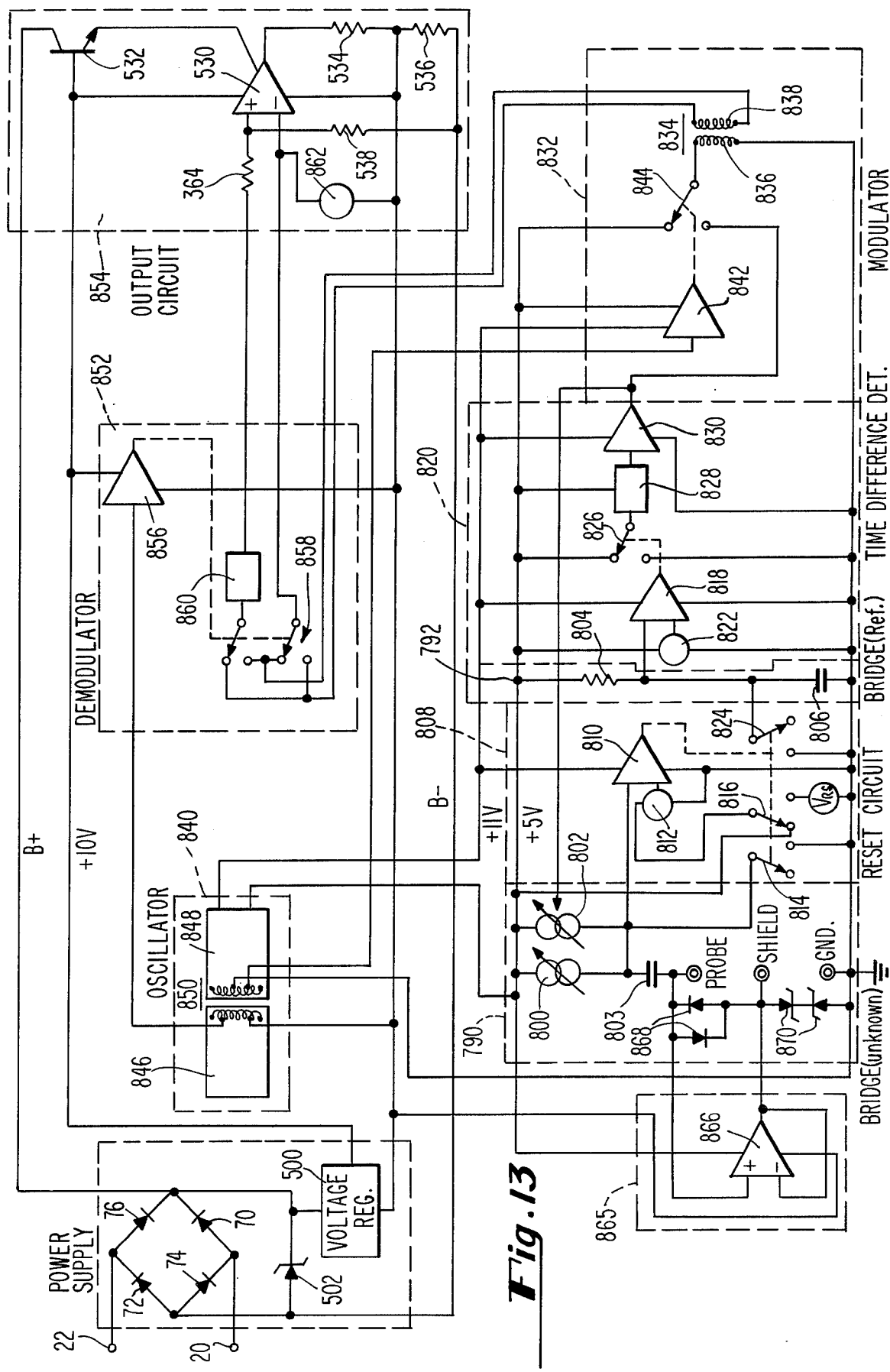
FIG. 13 is a block diagram of another two-wire transmitter representing another embodiment of the invention.

As shown in FIG. 13, the demodulator 852 comprises a synchronous rectifier depicted by an amplifier 856 and switch means 858 which demodulate the square wave produced at the secondary 838 of the transformer 834. The resulting full wave rectified voltage is applied to a low pass filter 860 to remove AC components prior to application to the output circuit 854.

The output circuit 854 comprises the amplifier 530 described in connection with the embodiment of FIGS. 11, 12a and 12b as well as the transistor 532 and the resistors 534, 536 and 538. In addition, the output circuit 854 comprises a bias network 862 connected between common and the inverting terminal of the amplifier 530 and a resistor 864 connected between the low pass filter 860 and the non-inverting terminal of the amplifier 530.

In the embodiment of FIG. 13, a shield buffer 865 is provided for use in conjunction with a shield terminal which serves as a guard electrode to prevent long cables and coatings from influencing the measurement of the admittance from probe to ground. The shield buffer 865 comprises an amplifier 866 having a non-inverting terminal connected to the probe terminal and the output of the amplifier 866 connected to the shield terminal so as to drive the shield or guard electrode at substantially the same potential as the probe so as to eliminate the effect of long cables and coatings on the measurement.

As also shown in FIG. 13, the unknown admittance side of the bridge 790 provides circuitry for protecting the probe and shield terminals. More particularly, a pair of parallel reverse poled diodes 868 are connected between the probe and shield terminals. In addition, a pair of reverse poled Zener diodes 870 are connected from the shield to ground. In this configuration, the shield tends to break up any stray coupling path through the diodes 868 and 870.

Figure 14A:
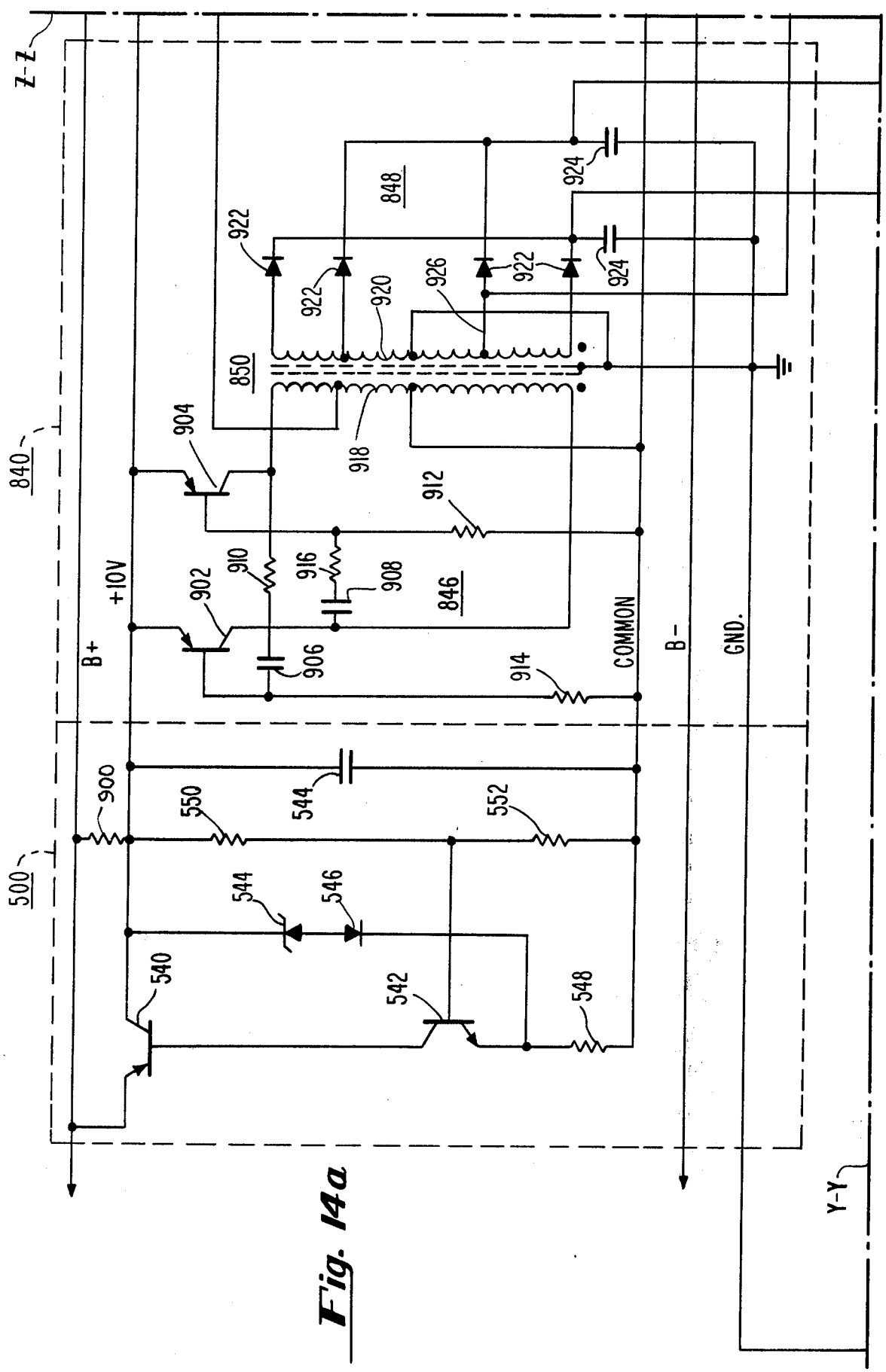
FIGS. 14(a-d) are schematic diagrams of circuitry shown in block form in FIG. 13 where the diagram has been split along lines y—y and z—z.

The embodiment of FIG. 13 will now be described in further detail with reference to FIGS. 14 (a-d). As shown in FIG. 14a, the voltage regulator 500 comprises substantially the same components as described with reference to the embodiments of FIGS. 11, 12a and 12b. In addition, the voltage regulator 500 comprises a start-up resistor 900 between the B+ line and the +10 volt line.

As also shown in FIG. 14a, the oscillator 840 comprises a multivibrator including transistors 902 and 904, capacitors 906 and 908, and resistors 910, 912, 914 and 916. The isolation transformer 850 which provides high voltage isolation between the portion 846 includes a transformer primary 918 which is directly connected to the two transmission lines and the portion of the oscillator circuit 848 comprising a secondary 920 which supplies the portion of the transmitter which is connected to the probe and ground. The output from the secondary 920 is rectified by diodes 922 and filtered by capacitors 924 so as to provide supply voltages for the +11 and +5 volt lines. A modulating signal is derived from a terminal 926 of the secondary 920 which is grounded at the center tap.

Figure 14B:
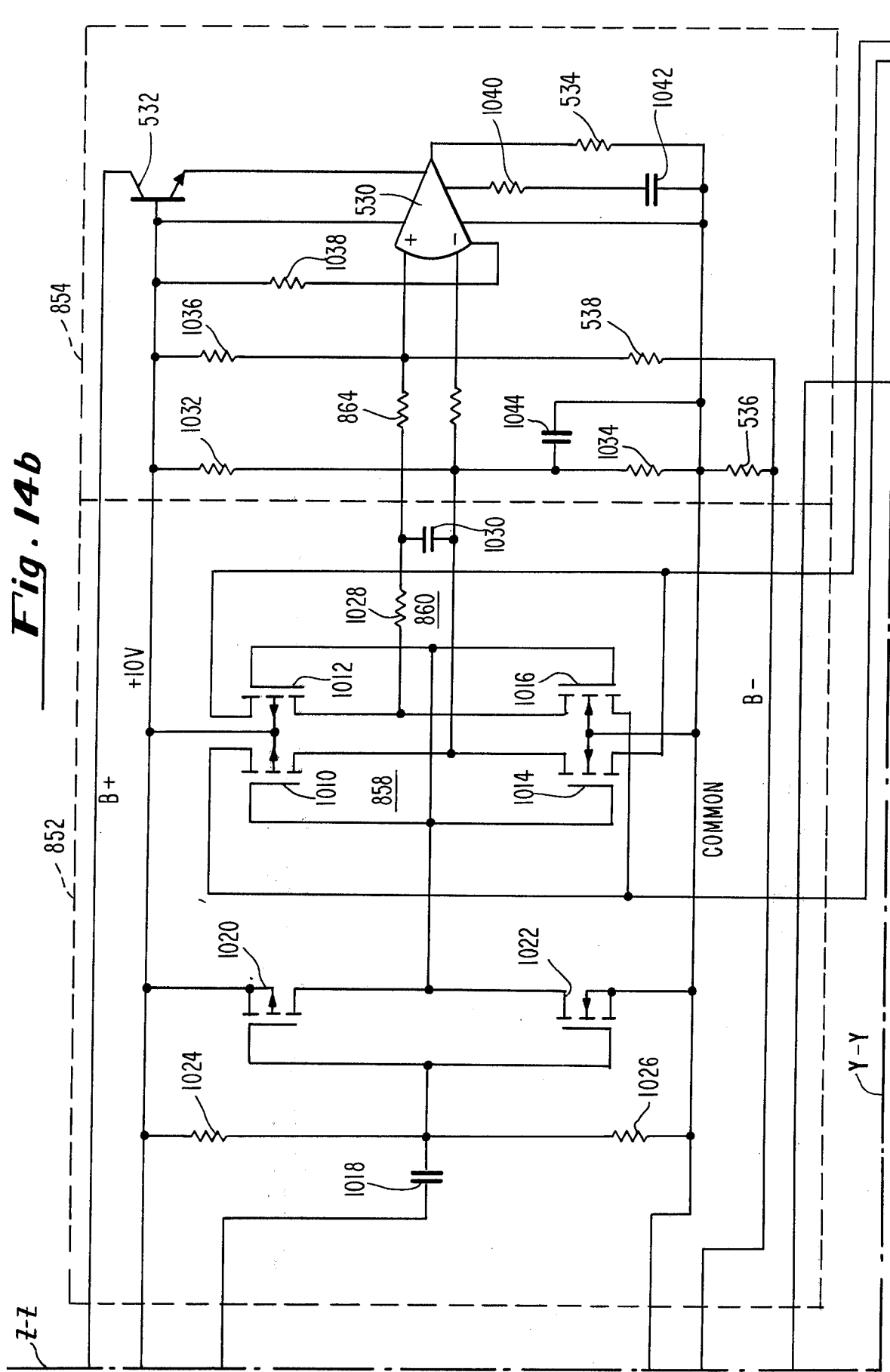
Figure 14C:
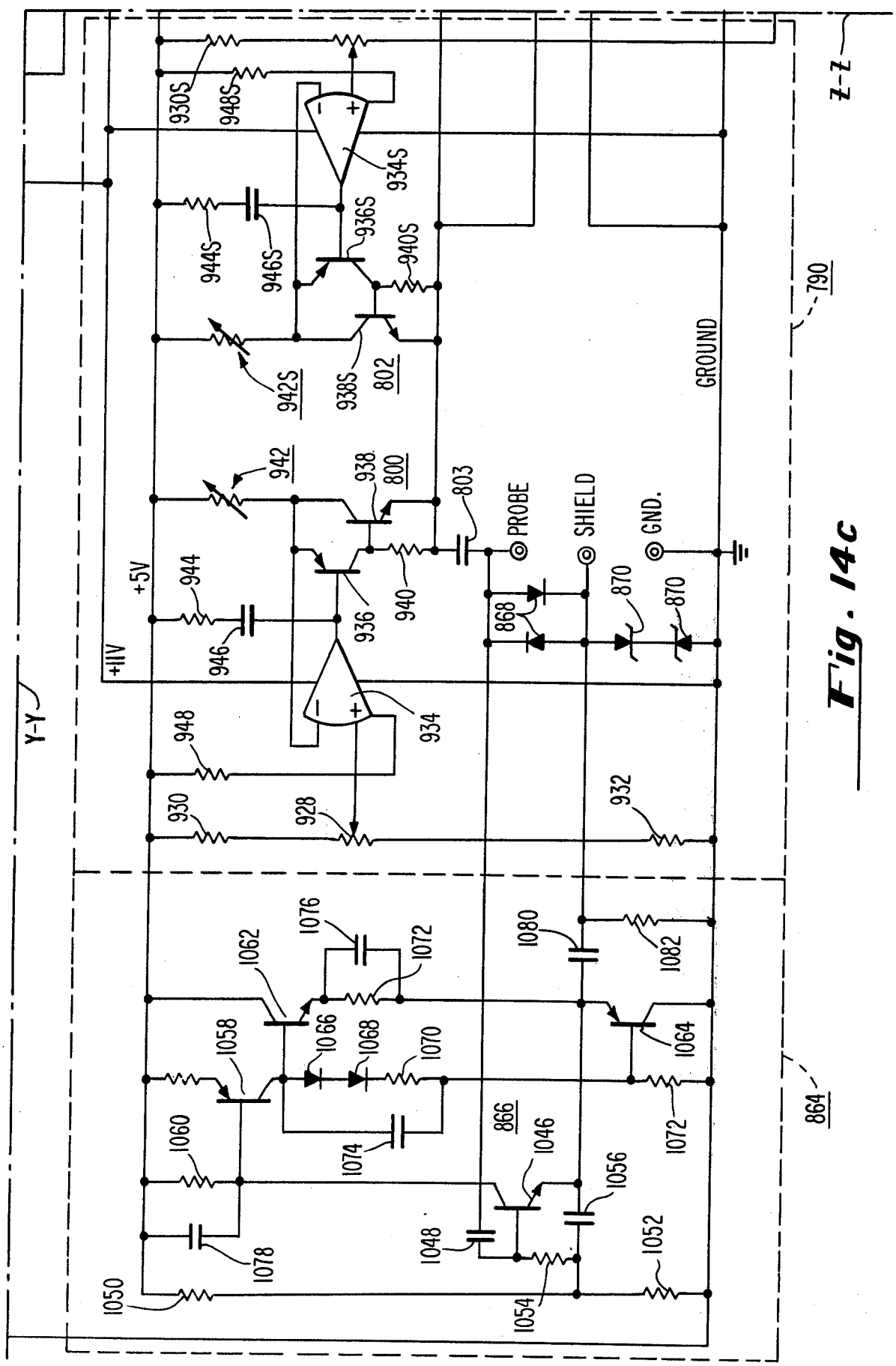

Referring now to FIG. 14c, the side 790 of the bridge which incorporates the unknown admittance from probe-to-ground will now be described in detail. As stated previously, the zero current source 800 and the span current source 802 are connected in series with the capacitor 803 and the unknown admittance from probe-to-ground. The zero current source 800 is controlled by a voltage picked off the +5 volt supply line by a fine zero potentiometer 928 which is connected in series with the resistors 930 and 932. The potentiometer 928 is connected to the non-inverting terminal of an operational amplifier 934 which has an output coupled to transistors 936 and 938 with the collector of the transistor 936 connected to the capacitor 803 through a resistor 940. The emitter of the transistor 936 and the collector of the transistor 938 are connected to a step zero resistance 942 (which has been shown as a potentiometer for simplicity). A feedback voltage is developed across the step resistance 942 which is applied to the inverting terminal of the operational amplifier 934. The current flow from the operational amplifier 934 will increase or decrease in response to changes in the variable resistance 942 so as to achieve a balance between the input at the inverting terminal and the input at the non-inverting terminal of the operational amplifier 934. In this connection, it will be understood that as the voltage from the fine zero potentiometer 928 goes more negative, a larger current will flow from the zero current source 800. The zero current source 800 further comprises a resistor 944 in series with a capacitor 946 which is connected between the output of the operational amplifier 934 and the +5 volt supply line. A supply resistor 948 is connected between the +5 volt supply line and the operational amplifier 934.

The span zero current source 802 comprises the same components as the zero current source 800. For the sake of brevity and simplicity, the same reference characters on FIG. 14b have been utilized with the addition of the letter "s" indicating a component of the span current source. The only difference between the span current source 802 and the zero current source 800 is the use of a feedback voltage at the non-inverting input of the operational amplifier 934s so as to maintain balance between the unknown admittance side 790 of the admittance bridge and the reference side 792 of the admittance bridge.

It will be noted that the operating controls for that portion of the transmitter which is connected to ground, i.e., fine zero, step zero, fine span and step span, are all direct current controls as contrasted with RF controls. More particularly, the operating controls comprise variable resistances in the zero current source and the span current source so as to adjust the charging rate of the unknown admittance probe to ground.

Figure 14D:
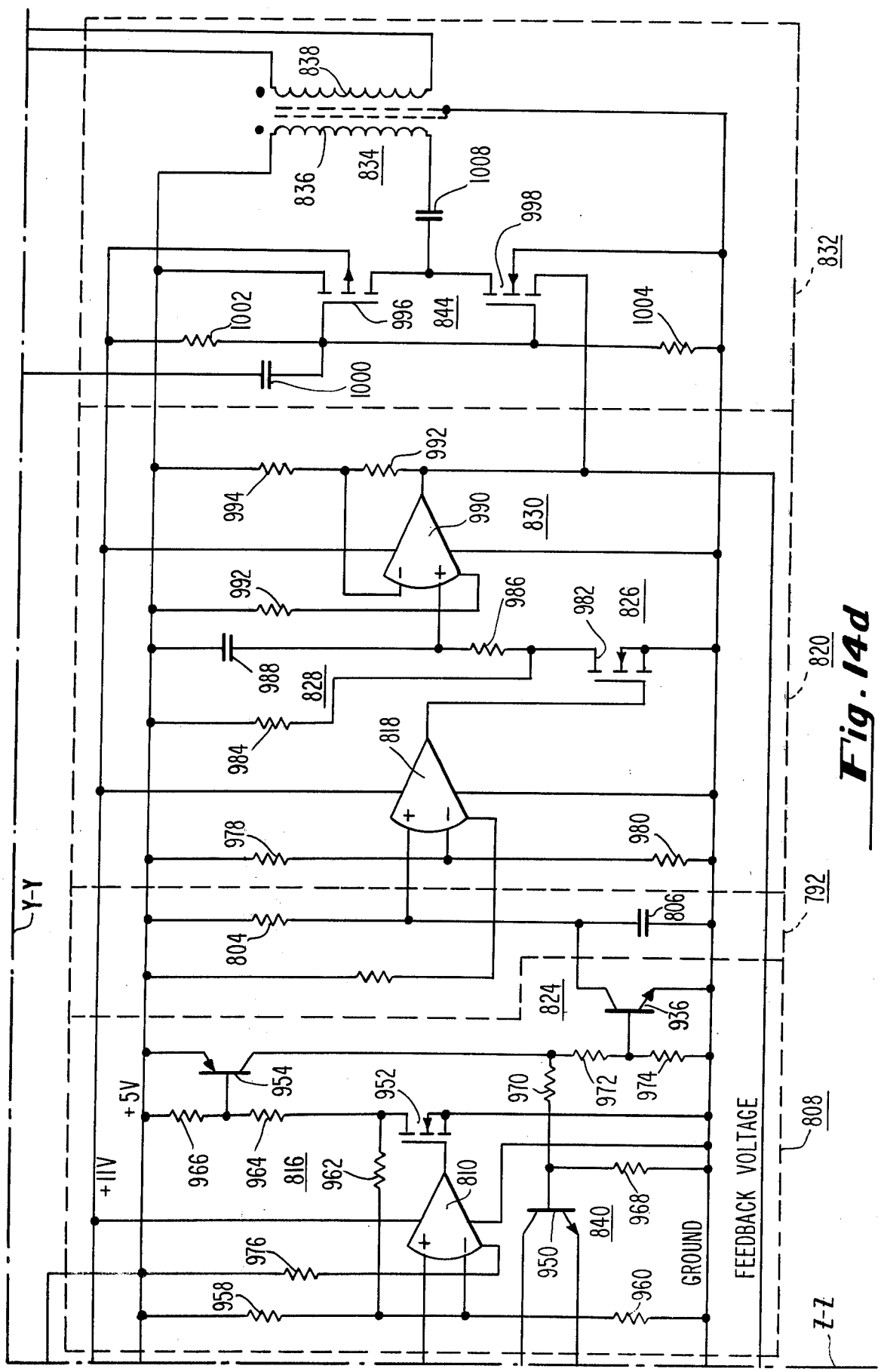

Referring to FIG. 14d, the reset circuit 808 comprises a transistor 950 which serves as the switch 840 which is coupled to the positive terminal of the comparator 810. A field effect transistor 952 in conjunction with a transistor 954 functions as the switch means 816 to control the negative input to the comparator 810. A transistor 956 connected across the reference capacitor 806 serves as the switch 824.

The operation of the reset circuit 808 is as follows. The zero current source 800 and the span current source 802 charge the capacitor 803 and the unknown admittance as shown in FIG. 14c until the voltage thereacross is equal to the voltage at the negative input of the comparator amplifier 810 as determined by the +5 volt supply in conjunction with resistors 958, 960, 962, 964 and 966. At this time, the comparator amplifier 80 turns on the field effect transistor 952 causing the reset function to be implemented and at the same time reducing the voltage on the negative input of the comparator amplifier 810 via the resistor 962 to a small voltage. Simultaneously, the transistor 954 turns on the transistor 950 which discharges the admittance formed by the capacitor in series with the unknown admittance until the voltage thereacross falls below the voltage present on the negative input of the comparator amplifier 810. The reset function is then terminated and the charge cycle repeats. The reset circuit also comprises resistors 968, 970, 972 and 974 which bias the transistors 950 and 956. In addition, a supply resistor 976 connects the comparator amplifier 810 to the +5 volt supply line.

As shown in FIG. 14d, the reference side of the bridge 792 comprises the reference capacitor 806 and the reference resistor 804. By providing a time constant for the reference side 792 of the bridge which is shorter than that of the current sources and the admittance formed by the capacitor 803 and the unknown admittance from probe to ground, the comparator amplifier 818 will trip before the comparator amplifier 810. The voltage across the capacitor 806 is compared with the voltage generated by the divider comprising resistors 978 and 980.

The switch 826 referred to in FIG. 13 comprises a field effect transistor 982 which is connected to the +5 volt supply line through a resistor 984 and to the positive input of the amplifier 990 through a resistor 986 which is also connected to the +5 volt supply line through a capacitor 988. When the comparator amplifier 818 is tripped, the voltage at the junction of the transistor 982 and resistors 986 and 984 will be pulled down toward ground. When the reset function is initiated, the transistor 956 in the reset circuit 808 will discharge the capacitor 806 to reset the voltage at the junction of the transistor 982 and resistors 986 and 984 will return to +5 volts. The resistor 986 and the capacitor 988 form the low pass filter 828 which filters the resulting square negative pulse in obtaining DC voltage proportional to the charge time difference between the reference half of the bridge 792 and the unknown reference side of the bridge 790.

The voltage across the capacitor 988 is amplified by an amplifier 990 which is supplied by the +5 volt supply line through a resistor 992. The gain of the amplifier 990 is proportional to the ratio of the sum of a feedback resistor 992 and a resistor 994 to the resistor 994 alone. The output from the amplifier 990 is fed back to the unknown side of the bridge 790, and more particularly, to the span current source 802 so as to control the amplifier 934s.

The output from the amplifier 990 is also chopped in the modulator 832 by the switch means 844 comprising field effect transistors 996 and 998. The modulation is synchronous with the drive from the isolating transformer 920 shown in FIG. 14a at the terminal 926 which is applied to the junction of the field effect transistors through a capacitor 1000. The bias at the junction of the field effect transistors 996 and 998 is derived from series connected resistors 1002 and 1004. The resulting square wave produced by the field effect transistors 996 and 998 is coupled to the isolating transformer 834 through a capacitor 1008.

The output from the secondary 838 of the transformer 834 is coupled to the demodulator 852 which will now be described with reference to FIG. 14b.

The square wave of varying amplitude which is coupled to the demodulator 852 is synchronously rectified by the switch means 858 comprising field effect transistors 1010, 1012, 1014 and 1016. The junction of the field effect transistors is driven by a square wave generated at the oscillator 840 which is coupled through a capacitor 1018 to the gates of field effect transistors 1020 and 1022. Resistors 1024 and 1026 bias the gates of the transistors 1020 and 1022. The resulting full wave rectified voltage is applied to the filter 860 comprising a resistor 1028 and a capacitor 1030. The DC output voltage from the filter 860 is fed to the output circuit 854 comprising the output amplifier 530, the transistor 532 and the resistors 864, 534, 536 and 538. The output circuit 854 also comprises a resistive bridge including resistors 1032, 1034 and 1036. The resistor 538 also forms part of this resistive bridge which is unbalanced in response to a positive voltage across the capacitor 1030. The resulting positive input to the amplifier 530 causes the output current to be increased and this output current is measured by the resistor 536 which develops a voltage proportional thereto. This voltage is placed in series with the resistor 538 thereby rebalancing the resistive bridge at the desired output current. In this way, the output current is held constant as a function of the voltage obtained from the demodulator 852. The current drawn by the output stage of the amplifier 530 is drawn through emitter follower transistor 532 from the B+ line, thereby avoiding any tendency of the output current to deregulate the 10 volt power supply. In this manner, any tendency of the output current to interfere with the operation of the other circuits is eliminated. The output circuit 854 further comprises a supply resistor 1038 and a series RC combination including a resistor 1040 and a capacitor 1042. A capacitor 1044 is connected in parallel with the resistor 1034. Referring now to FIG. 14c, the shield buffer 864 will be described. The base of a transistor 1046 forms a positive input to the shield buffer amplifier 866. The base receives the probe voltage through a capacitor 1048 where the operating point of the transistor 1046 is established by the resistive divider comprising resistors 1050, 1052 and 1054 which is boot-strapped to the output of the amplifier by a capacitor 1056. The negative input of the amplifier 866 comprises the emitter of the transistor 1046. The emitter is connected directly to the output providing 100% negative feedback for the amplifier 866. Thus the shunting effect of the resistor 1054 on the input of the amplifier 866 is reduced by the gain of the amplifier. The current drawn by the transistor 1046 is proportional to the error voltage, i.e., the voltage at the base minus the voltage at the emitter, times the forward transfer admittance of the transistor 1046. This current generates a voltage across the resistor 1060 and is amplified by a transistor 1058. The output voltage from the collector of the transistor 1058 is applied to the bases of transistors 1062 and 1064 which function as emitter followers so as to substantially reproduce the voltage at the output of the transistor 1058 at a much lower impedance. The emitter follower transistors operate Class A/B, and the standby bias current is established by series connected diodes 1066 and 1068 and resistors 1070 and 1072. The diodes 1066 and 1068 compensate for the base emitter voltage of the transistors 1062 and 1064. The resistor 1070 establishes the voltage which the transistors will maintain across the resistor 1072. Since the diodes and the transistor base-emitter junctions have similar temperature coefficients, the bias current will remain substantially unchanged as the temperature of the amplifier varies.

A capacitor 1074 maintains the same drive voltage at the base of both transistors while a capacitor 1076 maintains a low output impedance for positive as well as negative output currents. A capacitor 1078 forms the dominant pole of the amplifier 866 allowing its gain to roll off to unity below the frequency at which 180° phase shift is obtained. In this manner, the amplifier 866 is prevented from parasitic oscillation. The output of the amplifier 866 is coupled through a capacitor 1080 to the shield terminal so as to eliminate any DC from the shield and thereby prevent electrolytic corrosion of the shield electrode. A resistor 1082 is connected from the shield electrode to ground. Although a preferred embodiment of the invention has been shown and described, it will be understood that various modifications may be made without departing from the true spirit and scope of the invention as set forth in the appended claims.

What is claimed is:

1. In a two-wire transmitter system comprising a power supply and a load at one location and a two-wire transmitter at another location interconnected by a pair of transmission lines carrying a variable signaling current, the improvement comprising:
   an admittance sensing probe including a probe electrode adapted to sense the condition and corresponding admittance of materials;
   an admittance responsive network coupled to said probe representing the condition of materials; and output means coupled to said admittance responsive network for varying the signaling current in response to the condition of materials.

2. The transmitter of claim 1 wherein said admittance responsive network comprises:
first oscillator means comprising a first frequency determinative circuit including said admittance sensing probe, said first oscillator means generating a first signal changing frequency in response to changes in the admittance of said materials;
second oscillator means comprising a second frequency determinative circuit generating a second signal having a substantially constant reference frequency; and
frequency difference detector means coupled to said first oscillator means and said second oscillator means, said frequency difference detector means being coupled to said output means.

3. The transmitter of claim 2 wherein said admittance responsive network is supplied by said power supply through said pair of transmission lines.

4. The transmitter of claim 3 further comprising voltage regulating means coupled to said admittance responsive network for supplying a regulated voltage from said power supply to said admittance responsive network.

5. The transmitter of claim 4 further comprising spark protection means coupled to said pair of transmission lines.

6. The transmitter of claim 5 comprising a full wave rectifying bridge coupled to said pair of transmission lines so as to permit polarity reversals of said transmission lines when connecting the transmitter thereto.

7. The transmitter of claim 2 wherein said frequency difference detector means comprises means for digitizing the output from said frequency detector means.

8. The transmitter of claim 7 wherein said frequency difference detector means comprises comparator means for generating a difference signal representing the frequency difference between said first signal and said second signal.

9. The transmitter of claim 2 wherein said first oscillator means and said second oscillator means comprise a bridge-like circuit, one-half of said bridge-like circuit comprising said first frequency determinative circuit of said first oscillator means and the other half of said bridge-like circuit comprising said second frequency determinative circuitry of said second oscillator means, said second frequency determinative circuit including a reference admittance.

10. The transmitter of claim 9 comprising a probe cable coupled to said probe and a compensate terminal associated with said second oscillator means, and a cable matched to a probe cable connected to said compensate terminal.

11. The transmitter of claim 2 wherein said output means comprises means for generating a feedback signal substantially proportional to the signal current.

12. The transmitter of claim 2 wherein the admittance of said admittance sensing probe is DC isolated from said first oscillator means.

13. The transmitter of claim 1 wherein said admittance responsive network comprises:
first admittance means coupled to said sensing probe so as to include the admittance of said materials;
second admittance means comprising a reference admittance;
charge current means coupled to said first admittance means and said second admittance means for charging thereof;
discharge means coupled to said first admittance means and said second admittance means for discharging thereof; and
charge rate detection means for detecting the difference in charging rates between said first admittance means and said second admittance means.

14. The transmitter of claim 13 wherein said charge current means comprises a first zero current source and a second span current source.

15. The transmitter of claim 13 wherein said first admittance means and said second admittance means comprises an admittance bridge.

16. The transmitter of claim 15 wherein said first admittance means forms a first side of said bridge and said second admittance means forms a second side of said bridge, said charge rate detection means detecting a difference in time to charge said first side as compared with said second side.

17. The transmitter of claim 16 wherein said bridge and said charge current means are DC isolated from said transmission lines.

18. The transmitter of claim 17 wherein charge current means comprises means for adjusting the DC charging current by adjusting DC current flow.

19. The transmitter of claim 16 further comprising feedback means coupling said charge rate detection means to said current source means for rebalancing said bridge.

20. The transmitter of claim 13 including guard means and guard amplifier means having an input coupled to said sensing probe and an output coupled to said guard means for driving said guard means at substantially the same potential as said sensing probe.

21. The transmitter of claim 20 comprising parallel reverse poled diodes coupled between said sensing probe and said guard means and a pair of series reverse poled Zener diodes coupled between said shield means and ground.

22. The transmitter of claim 13 wherein said admittance responsive network is supplied by said power supply through said pair of transmission lines.

23. The transmitter of claim 22 wherein said output means comprises means for generating a feedback signal substantially proportional to the signal current.

24. The transmitter of claim 23 wherein said output means comprises modulator means coupled to said charge rate detection means for generating an AC signal representing the feedback signal, demodulator means for demodulating the modulated AC signal, DC isolation means for coupling demodulator means to said modulator means, and output amplifier means coupled to said demodulator means, said output amplifier means being coupled to said pair of transmission lines so as to control the current drawn by said two-wire transmitter.

25. The transmitter of claim 13 including spark protection means coupled to said admittance sensing probe.

26. The transmitter of claim 25 including guard means associated with said probe, said spark protection means coupled between said probe and said guard and said guard means and ground such that said guard means functions to break up the stray path comprised of the protecting devices.

27. The transmitter of claim 13 including spark protection means coupled to said transmission lines.

28. The transmitter of claim 13 further comprising:

oscillator means coupled to said pair of transmission means;

DC power supply means including rectifying means coupled to said admittance responsive network; and transformer means coupling said oscillator means to said DC power supply means.

29. The transmitter of claim 1 wherein said output means comprises an output amplifier including a voltage feedback network including a resistor through which DC current drawn by the two-wire transmitter flows so as to stabilize the flow of the current at all current levels.

30. The two-wire transmitter of claim 1 further comprising a full wave rectifying bridge coupled to said pair of transmission lines for permitting current to flow through one pair of diodes when the terminals are connected to the transmission wires with one polarity and current to flow through the other pair of diodes when the terminals of the bridge are connected to the transmission wires with the opposite polarity.

31. The transmitter of claim 1 wherein said admittance responsive network comprises a bridge having an unknown admittance representing the condition of materials on one side of said bridge and a reference admittance on the other side of the bridge.

32. The transmitter of claim 31 including span adjustment means associated with said bridge.

33. The transmitter of claim 31 including zero adjustment means associated with said bridge.

34. The transmitter of claim 1 further comprising a regulated power supply coupled to and supplied by said transmission lines.

35. The transmitter of claim 1 wherein the admittance of said admittance sensing probe is DC isolated from said transmission lines.

* * * * *

UNITED STATES PATENT AND TRADEMARK OFFICE
CERTIFICATE OF CORRECTION

PATENT NO. : 4,146,834

DATED : March 27, 1979

INVENTOR(S) : Frederick L. Maltby et al

It is certified that error appears in the above-identified patent and that said Letters Patent are hereby corrected as shown below:

Column 1, line 27, delete "transmitte" and insert --transmitter--.

Column 1, line 32, delete "stance" and insert --stances--.

Column 4, line 49, after "second side" insert --.-- .

Column 5, line 16, delete "digram" and insert --diagram--.

Column 5, line 65, delete "34" and insert --24--.

Column 16, line 31, delete "zero step" and insert --step zero--.

Column 16, line 41, delete "varations" and insert --variations--.

UNITED STATES PATENT AND TRADEMARK OFFICE
CERTIFICATE OF CORRECTION

PATENT NO. : 4,146,834
DATED : March 27, 1979
INVENTOR(S) : Frederick L. Maltby et al It is certified that error appears in the above-identified patent and that said Letters Patent are hereby corrected as shown below:

Column 16, line 65, "A differentiating network 524 is coupled..." starts a new paragraph.

Column 19, line 10, delete "stabiize" and insert --stabilize--.

Column 20, line 41, delete "miliampere" and insert --milliampere--.

Column 24, line 36, delete "80" and insert --810--.

Column 26, line 51, "Although a preferred" should start a new paragraph.

Signed and Sealed this

Fifth Day of August 1980

[SEAL]

Attest:

SIDNEY A. DIAMOND

Attesting Officer

Commissioner of Patents and Trademarks

REEXAMINATION CERTIFICATE (1798th)
United States Patent [19]
Maltby et al.

[11] B1 4,146,834
[45] Certificate Issued Sep. 22, 1992

[54] ADMITTANCE MEASURING SYSTEM FOR MONITORING THE CONDITION OF MATERIALS

[75] Inventors: Frederick L. Maltby, Jenkintown; Jonathan Kramer; Kenneth M. Loewenstern, both of Warminster, all of Pa.

[73] Assignee: Drexelbrook Controls, Inc.

Reexamination Request:
No. 90/002,405, Aug. 21, 1991

Reexamination Certificate for:
Patent No.: 4,146,834
Issued: Mar. 27, 1979
Appl. No.: 743,618
Filed: Nov. 22, 1976

Certificate of Correction issued Aug. 5, 1980.

Related U.S. Application Data

[63] Continuation-in-part of Ser. No. 507,540, Sep. 19, 1974, Pat. No. 3,993,947.

[51] Int. Cl.[5] .............. G01R 11/52; G01R 27/26
[52] U.S. Cl. .................. 324/610; 324/678; 324/681; 340/870.16; 340/870.39
[58] Field of Search .......... 324/610, 649, 650, 651, 324/652, 658, 663, 664, 666, 668, 675, 680, 682, 686, 690, 689, 691, 693, 706, 708, 725, 678, 681; 340/870.16, 870.39

[56] References Cited
U.S. PATENT DOCUMENTS

2,785,374 3/1957 Fay et al. .
3,646,538 2/1972 Frick .
3,648,165 3/1972 Shawhan .
3,680,384 8/1972 Grindheim .
3,706,980 12/1972 Maltby .
3,781,672 12/1973 Maltby et al. .
3,993,947 11/1976 Maltby et al. .

FOREIGN PATENT DOCUMENTS

1335349 10/1970 United Kingdom .
1528167 9/1975 United Kingdom .

OTHER PUBLICATIONS

Control & Instrumentation, Sep. 1970, p. 57, "Liquid Level Transmitter".
Industrie Post, Jan. 1971, p. 22 with verified English language translation.
Drexelbrook Engineering Co., Document 408-6200 dated Nov. 18, 1975.

*Primary Examiner*—Jack B. Harvey

[57] ABSTRACT

A two-wire transmitter includes an admittance sensing probe adapted to sense the conditions and corresponding admittance of materials. The probe is coupled into an admittance responsive network which generates an admittance signal representing the condition of materials. The output current from the transmitter is varied in response to the admittance signal. In one embodiment of the invention, the admittance responsive network comprises a variable frequency oscillator whose frequency varies with the admittance of the materials. In another embodiment, the admittance responsive network comprises a ramp generator with a frequency which varies with the admittance of the materials. In another embodiment, the admittance responsive network comprises a bridge whose balance changes in response to the admittance of the materials.

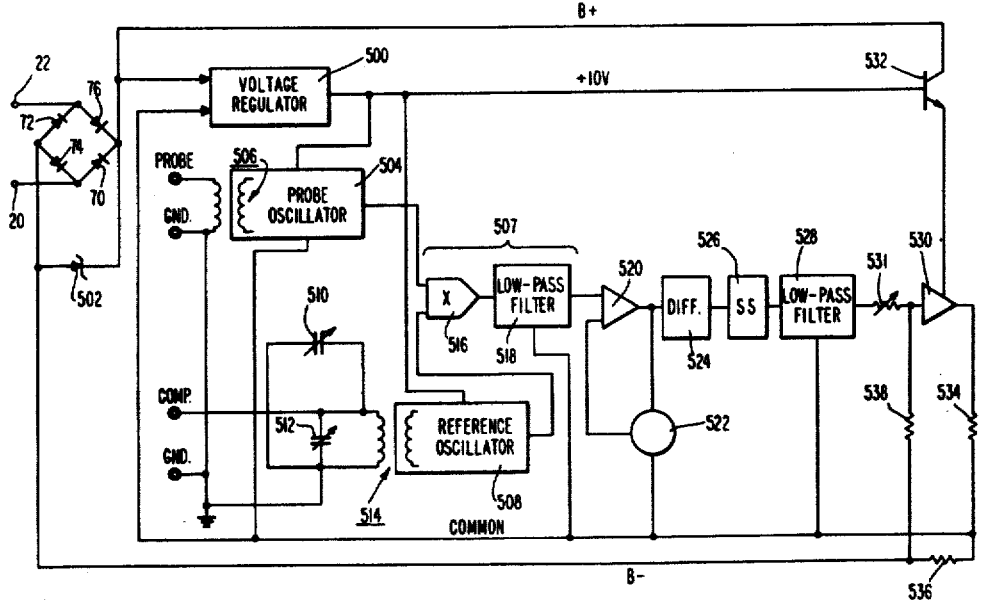

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-35 is confirmed.

* * * * *